(12) United States Patent
Nadler et al.

(10) Patent No.: US 7,166,441 B2
(45) Date of Patent: Jan. 23, 2007

(54) METHOD AND APPARATUS FOR THE IDENTIFICATION AND QUANTIFICATION OF BIOMOLECULES

(75) Inventors: Timothy K. Nadler, Framingham, MA (US); Kenneth G. Parker, Hopkinton, MA (US); George J. Vella, Medway, MA (US); Barrie G. Wagenfeld, Saugus, MA (US); Yulin Huang, Westwood, MA (US); Robert J. Lotti, East Boston, MA (US)

(73) Assignee: PerSeptive Biosystems Inc., Framingham, MA (US)

(*) Notice: Subject to any disclaimer, the term of this patent is extended or adjusted under 35 U.S.C. 154(b) by 548 days.

(21) Appl. No.: 10/327,342

(22) Filed: Dec. 20, 2002

(65) Prior Publication Data

US 2003/0175844 A1    Sep. 18, 2003

Related U.S. Application Data

(60) Provisional application No. 60/363,663, filed on Mar. 12, 2002.

(51) Int. Cl.
*C12Q 1/37* (2006.01)

(52) U.S. Cl. .......................................... 435/23; 204/464

(58) Field of Classification Search ...................... None
See application file for complete search history.

(56) References Cited

U.S. PATENT DOCUMENTS

| | | | |
|---|---|---|---|
| 5,760,393 | A | 6/1998 | Vestal et al. |
| 5,808,300 | A | 9/1998 | Caprioli |
| 6,221,626 | B1 | 4/2001 | Bienvenut et al. |
| 6,348,688 | B1 | 2/2002 | Vestal |
| 6,441,140 | B1 | 8/2002 | Comb et al. |
| 2002/0012920 | A1 * | 1/2002 | Gardner et al. ................ 435/6 |

FOREIGN PATENT DOCUMENTS

CA    2244947 A1 * 12/1999

WO    WO 00/45168    8/2000

OTHER PUBLICATIONS

Binz et al, "A Molecular Scanner To Automate Proteomic Research and To Display Proteome Images", Anal. Chem. 1999, vol. 71, pp. 4981-4988.*
Berggren et al., Proteomics 1: 54-65 2001.
Gygi et al., Natl. Biotechnol 17: 994-999 1999.
Klarskov et al., Rapid Comm. In Mass Spect. 16: 35-42 2002.
Pluskat et al., Multiwell In-Gel Protein Digestion and Microscale Sample Preparation For Protein Identification By Mass Spectrometry 2: 145-150 2002.
Tonge et al., Proteomics 3: 377-396 2001.
Veenstra et al., J. Am. Soc. Mass Spectrom 11: 78-82 2000.
Vestal et al., Mass Spectrometry in Biology and Medicine 1-16 2000.
PCT Search Report for US03/06615.

* cited by examiner

*Primary Examiner*—Christopher R. Tate
*Assistant Examiner*—Amanda P. Wood
(74) *Attorney, Agent, or Firm*—Andrew T. Karnakis

(57) ABSTRACT

Polypeptides are electroblotted through a digestion membrane to a composite capture membrane that can be directly analyzed using mass spectrometry. The molecular weights of the fragments generated by the digestion membrane are then used to identify the polypeptide from which they originated. The digestion membrane contains an immobilized protease such as trypsin, which cleaves the electroblotted polypeptides into fragments during electroblotting with such high enzyme cleavage capacity and efficiency that one pass of the polypeptide through the membrane is sufficient. The peptide fragments are collected onto a composite capture membrane that is chemically treated, for example by adding a mixture of nitrocellulose and MALDI matrix, so as to absorb peptides near the surface to facilitate desportion, thereby increasing the sensitivity of subsequent analysis by MALDI-TOF mass spectrometry. A wide variety of application are disclosed including identifying proteins separated on a gel or within a tissue sample.

16 Claims, 14 Drawing Sheets

FIG. 8b
FIG. 8a

METHOD AND APPARATUS FOR THE IDENTIFICATION AND QUANTIFICATION OF BIOMOLECULES

CROSS REFERENCE TO RELATED APPLICATION

This application claims priority to U.S. Provisional Patent Application No. 60/363,663, filed Mar. 12, 2002, the entire contents of which are incorporated by reference herein.

BACKGROUND OF THE INVENTION

1. Field of the Invention

This invention generally relates to a method and apparatus for identifying or quantifying polypeptides. More specifically, this invention can be used to identify or quantify polypeptides that have been separated using a porous support, for example, using polyacrylamide gel electrophoresis (PAGE). The present invention can also be used to identify unseparated proteins from any other 1 or 2-dimensional array of proteins, for example, proteins absorbed onto a membrane, as in a tissue slice or organ blot, or from cells growing on a bacterial or tissue culture plate, or from a microtiter plate containing proteins from 1 or 2-dimensional gels or chromatography fractions. The technique involving separated polypeptides is especially useful in biochemical studies where the goal is to rapidly identify or quantify tens to hundreds of the most abundant proteins in a biological sample, while retaining some information about the starting molecular weight of the proteins that are identified. The technique that does not involve pre-separating polypeptides can be used to determine which proteins are the most abundant in different sections of any two-dimensional protein array. Relative quantification of separated proteins from one or more samples is accomplished by using stable isotope labeling of the proteins prior to separation, electroblotting, digestion and mass analysis.

2. Description of the Related Art

Biochemists often are interested in establishing the major protein constituents of biological samples, and commonly are interested in knowing which proteins have changed between an experimental sample and a control sample. In the last decade, gel electrophoresis followed by peptide mass fingerprinting (PMF) or tandem (MS-MS) mass spectrometry have become the methods of choice to perform these analyses. Typically, gel electrophoresis is performed to separate the proteins, and the whole gel is stained with Coomassie brilliant blue. After studying the gel pattern, the scientist determines which slices are to be analyzed. Manual or robotic methods are then used to excise the pieces of gel containing the protein(s) of interest. After several rounds of washing, the whole gel slice is separately digested with a protease, commonly trypsin, and the digestion products are extracted from each gel slice, concentrated, desalted, and submitted separately to mass spectrometric analysis. The mass spectra are often collected in a fully automated way, and special software is commercially available to make automatic protein identifications. The robots that perform the initial sample preparation steps are also commercially available, but are costly. In addition, the scientist must keep track of how each sample was related to the original gel during all of these steps, which introduces many opportunities for confusion. In many cases, the samples become accidentally contaminated with exogenous contaminants to differing degrees during these processes. These processes typically require several days to perform, including typically an overnight protease digestion step. Because these techniques are laborious and require a high degree of operator training, protein identifications of this kind are performed mainly by large pharmaceutical companies and by core laboratories that charge the original researcher a sizable amount per slice analyzed. In addition, these techniques are inefficient for identifying proteins in nearby slices because the cutting out of the polypeptide bands from the gel must be done sequentially, and the excision process may shift the gel making subsequent excision steps difficult to control. Also, losses occur when the polypeptides adhere to the walls of the tube.

Quantification is typically carried out on the proteins either before or after they are separated on the gel. There are three methods typically used:

1. Staining with Coomassie or silver stain or fluorescent dyes: At the present time this requires the soaking of the gel in a solution containing protein staining compounds that are visualized in visible light or ultraviolet light after washing away the excess dye from the gel, a process that typically takes tens of minutes to hours.
2. Tagging proteins before separation: Fluorescent proteins derivatives can be made by reacting the proteins with fluorescent dyes prior to separation on a gel. The nature of the fluorescent dye may alter the mobility of the protein derivative during separation on the gel, however, thereby resulting in error. After separation, the fluorescence intensity is measured as described, for example, by Berggren et al., Proteomics 1: 54–65 2001; and Tonge et al., Proteomics 3: 377–396 2001.
3. Tagging proteins with radioactive isotopes: Radio-labeling of proteins prior to separation is commonplace. Visualization is typically done by exposure of the gel containing the separated radio-labeled proteins to photographic film. The amount of exposure is relative to the amount of radioactivity on the protein. However, use of radioactive tags is undesirable because of regulatory considerations regarding access to, exposure to, and disposal of radioactive materials. In addition, many proteomic samples (e.g., serum samples) can not be biosynthetically labeled, and additional chemistry must be performed to introduce radioactivity into the sample.

All three of the foregoing methods require additional steps to stain, destain, wash, and image, which means that more time is required to obtain the results. Quantitative measurements require comparisons to standard proteins labeled in the same fashion and separated in the same manner; thus additional experiments need to be done.

Recently, due to increases in the resolution of matrix assisted laser desorption ionization-time of flight mass spectrometers (MALDI-TOF MS), it has become possible to use heavy stable isotopes for quantitative purposes. In these experiments, a control sample contains proteins that are labeled with normal amino acids, whereas the experimental sample contains proteins that contain heavy isotope enriched atoms (or vice versa), particularly deuterium, C-13, N-15 and O-18 (see Veenstra et al., J Am Soc Mass Spectrom 11: 78–82 2000). The two samples are mixed together prior to protein or peptide separation, and then distinguished by the mass spectrometer. Alternatively, the heavy atoms are added to specific amino acid side-chains by using protein modification reagents that have come in two different isotopic forms as described by Gygi et al, Nat. Biotechnol 17: 994–999 1999. In this case, the chemical modification step can take place either before or after protein digestion. In many cases, isotope enrichment strategies have avoided gels altogether because of the difficulties of the sample processing steps described above. Instead, the proteins are digested as one sample prior to peptide separation, and protein identification is performed at the level of individual peptides, using MS—MS techniques. This technology is not commonly used when the goal is to determine the relative quantification of a limited number of proteins because of reasons of expense. In addition, all information about the starting molecular weight of the proteins is lost when the proteins are digested at the beginning of the experiment, and intact molecular weight is often of crucial interest to biochemists.

A second, unrelated protein analysis technique involves the direct identification of proteins from whole tissues or colonies. In the past, proteins were typically extracted from colonies, tissues and tissue slices by physical disruption of the cells that make up the sample. However, as disclosed in U.S. Pat. No. 5,808,300, it is now possible to analyze proteins that are ablated directly from tissues by mass spectrometry. However, intact proteins are nearly impossible to identify compared to their peptide counterparts.

Recently, a technique for effecting parallel protein identifications, called the molecular scanner, that does not require gel staining, spot excision and extraction and peptide isolation was described in U.S. Pat. No. 6,221,626. An electroblotter sandwich was described comprising a hydrophilic membrane containing an immobilized protease positioned between an electrophoresis gel and a hydrophobic collection membrane which absorbed peptide fragments. The hydrophobic membrane was later treated with a MALDI ionizable matrix that permitted MALDI analyses of the cleaved polypeptide immobilized samples directly from the membrane. Thus all of the proteins that were present in the gel are processed simultaneously using techniques that are compatible with mass spectrometry. In this patent, the electrical current used to drive the peptide fragments to the collection membrane was either pulsed or was alternating current, which required special electroblotting equipment. In addition, this mode of electrical current use is undesirable since it increases the time needed to process samples. This technique was subsequently refined as described in published PCT patent application WO 00\45168 to include an in-gel digestion step. However, neither of these two techniques was completely satisfactory for certain applications. For example, there were technical difficulties in obtaining consistent and sensitive mass signals using the original techniques described above. Also, no techniques were described that allowed simultaneous protein identification and the use of heavy isotopes for protein quantification. These limitations have made it both less desirable and more difficult for biochemists to use the molecular scanner on a casual basis. Both the '626 patent and the published PCT patent application WO 00/45168 described above are incorporated herein by reference.

Accordingly, it would be desirable to provide a method and apparatus for performing molecular scanner experiments that do not require any specialized equipment, so that this technique can be applied to routine biochemical analyses. In addition, it would be desirable to develop a means to use heavy isotopes for protein quantification without losing all information about the protein's starting molecular weight in the sample. The method and apparatus that we describe below fulfills these requirements.

SUMMARY OF THE INVENTION

The present invention relates to the identification or quantification of polypeptides from a protein sample. In one embodiment proteins are separated on a gel and cleaved into peptide fragments by digestion with an enzyme during electroelution. Peptide fragments can then be deposited on the surface of a composite capture membrane.

In one embodiment, a composite capture membrane for collecting peptide fragments is prepared so that the captured fragments are concentrated on an outside surface of the composite capture membrane adjacent to the digestion membrane. This is accomplished by pre-treating a PVDF membrane modified with a quaternary amine with a combination of nitrocellulose and MALDI matrix.

In one embodiment, proteins are labeled with heavy stable isotopes to provide for the relative quantification of proteins. The technique of labeling the amino groups of lysine residues with deuterated or non-deuterated acetyl groups is compatible with sodium dodecyl sulfate (SDS)-PAGE and allows simultaneous relative protein quantification.

In one embodiment, a focusing technique causes the digested polypeptides to be deposited onto a discrete zone on the capture membrane. In this manner it is not necessary to scan the whole membrane to find the electro-deposited peptides.

In one embodiment of the molecular scanner described herein, the cleavage agent is immobilized and interposed as the "filling" in an electroblotting "sandwich" between a support such as the separation gel or from a gel previously contacted with animal tissue as one "slice" of the sandwich and a composite capture membrane, exemplified as a conventional polyvinylidene difluoride (PVDF) membrane, appropriately modified in accordance with the present invention, as the other "slice" of the sandwich. In this way, the fragments are collected on the surface of the composite capture membrane and can then be formulated in an appropriate way for the MALDI-TOF MS. It is only necessary that the electroblotting is carried out so that the proteins have a sufficiently long residence period in the proximity of the immobilized cleavage agent to ensure that a reasonable amount of the fragments is produced but not so long as to allow undesired diffusion. This is easily achievable by adjusting the voltage and buffer solution used in the electroblotting. Furthermore, high enzymatic activity is obtained by immobilizing the cleaving enzyme securely on the hydrophilic membrane, while minimizing autodigestion (cleavage of the enzyme by itself).

The present invention also reduces the time presently necessary for performing analyses of the type described herein so that the entire analysis, from gel to the beginning of mass spectrometric analysis, can be performed in a single day. The same device can be used to analyze polypeptides from other sources than gels, for example, tissue blots or tissue slices, chromatographic fractions, spots cored from 2D gels, etc. The simplicity of this system for accomplishing parallel protein digestions and capture onto surfaces suitable for direct MALDI analyses makes it attractive as a sample preparation method for the analysis of spots or slices excised from gels, or for protein fractions of any kind.

BRIEF DESCRIPTION OF THE DRAWINGS

FIGS. 8a and 8b show a tissue image of a chicken heart derived with the use of the present invention.

DESCRIPTION OF THE PREFERRED EMBODIMENTS

Figure 1:
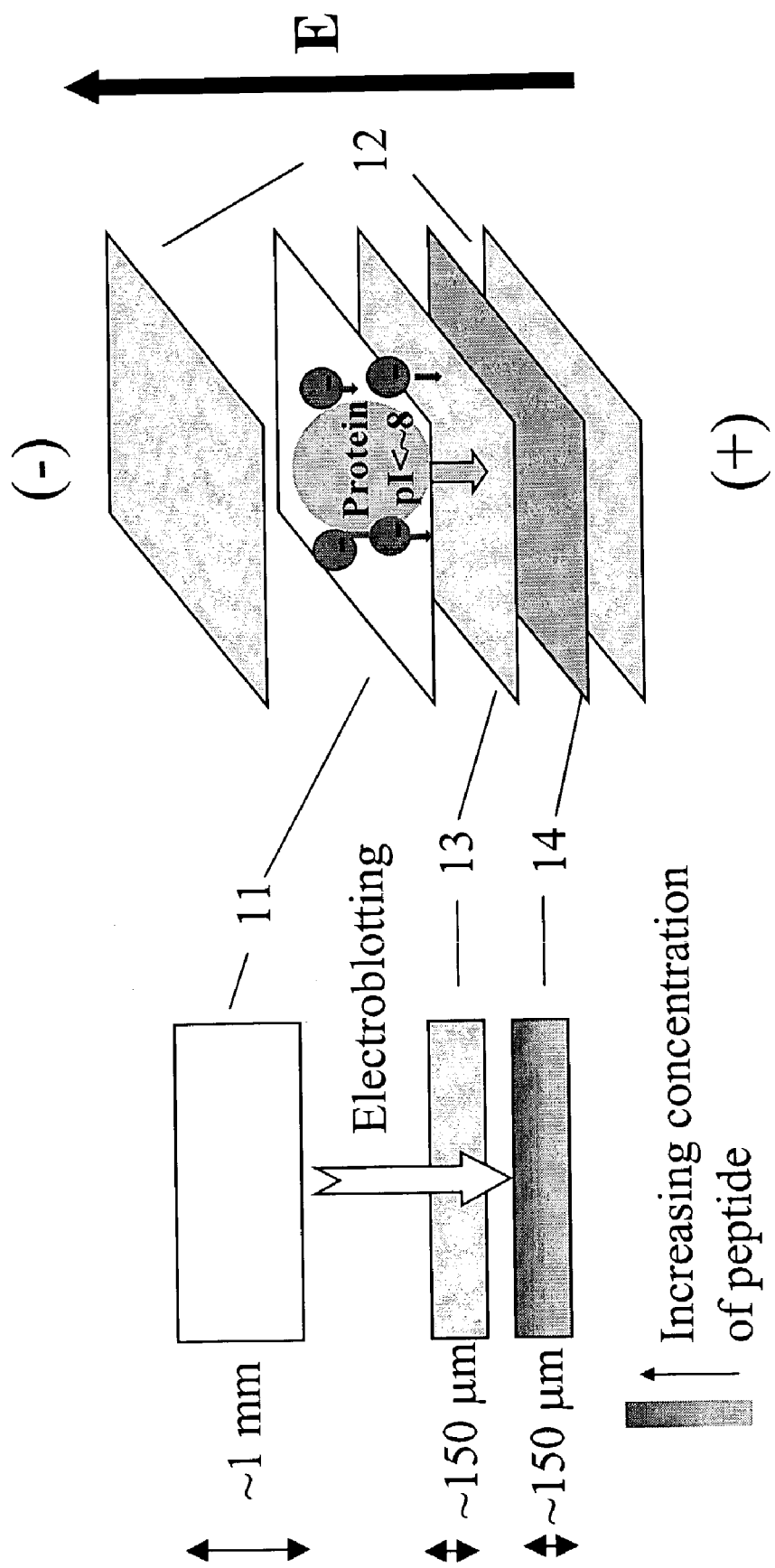
FIG. 1 is a schematic view of one embodiment of blotting "sandwich" which can be used in the invention.

The present invention provides an improved method and apparatus for immobilizing the cleavage agent and for forming the composite capture membrane. This permits the polypeptide that is to be cleaved to pass in contact with the cleavage agent continuously in a single pass rather than discontinuously either in one direction or in two directions. Furthermore, it is not necessary to start the digestion process in the separating gel prior to electroblotting as was previously described in published PCT Patent Application WO 00/45168.

The immobilized cleavage agent has a higher capacity to effect peptide fragment formation than the immobilized cleavage agent of the prior art. In addition, the composite capture membrane is formed by a procedure which assures that the peptide fragments are isolated on the surface of the composite capture membrane facing the hydrophilic membrane rather than within the interior of the composite capture membrane.

According to a specific aspect of the invention there is provided improved methods of identifying polypeptides which have been separated by gel electrophoresis or blotted onto a membrane from a one or two dimensional array of proteins, for example an intact tissue, or bacterial cell culture as follows:

a) providing adjacent to the gel at least one hydrophilic membrane on which is immobilized at least one reagent capable of cleaving a polypeptide. In the case of a protease, the hydrophilic membrane is treated with the addition of high salt concentrations and a protease inhibitor in order to deposit high concentrations of the protease while minimizing protease autodigestion.

b) providing a composite capture membrane suitable for receiving thereon fragments of polypeptide transferred thereto by electroblotting. The composite capture membrane is positioned beyond the hydrophilic membrane in a direction of movement of the peptide fragments of polypeptide (usually cathode to anode). The composite capture membrane is modified by the addition of compounds that promote peptide capture such as nitrocellulose and a matrix material which promotes ionization of peptides for MALDI analysis such as alpha cyano-4-hydroxycinnamic acid (HCCA).

c) electroblotting the polypeptides from the separation gel through the hydrophilic membrane or membranes, under conditions effective to cause the polypeptides to be cleaved into fragments by the cleavage reagent, to the composite capture membrane. This step occurs during a single pass under constant unidirectional electrical current.

d) identifying the fragments collected on the composite capture membrane by MALDI-TOF MS and MALDI-TOF MS-MS and from the identification of the fragments, identifying the polypeptide from which they originated.

The method can be further extended by:

e) providing relative quantification of the polypeptides identified by labeling the proteins prior to separation with reagents differentially containing stable isotopes that can be distinguished by mass spectrometry. For example, intact proteins can be treated with N-hydroxysuccinimyl-acetate (NHSA), which reacts with lysine side-chains. The NHSA can be synthesized with the acetate labeling group containing either 3 deuterium atoms or 3 hydrogen atoms. The samples are then mixed together prior to gel electrophoresis, digestion, capture, and MS analysis. The relative amount of the proteins in the control compared to the experimental sample can then be deduced by measuring the relative intensities of each pair of peptides as measured by MS. For each protein, the majority of peptides that are detected will be in the form of these pairs (the major exceptions being peptides that terminate with arginine residues and that also are preceded by arginine residues), which means that the expression level of each protein will be based on many individual peptide measurements.

Furthermore, the method thus described is equally applicable to the analysis of proteins derived from tissues and tissue slices or cell culture.

In another aspect, the invention provides a method to produce a membrane suitable for use in an electroblotting sandwich, having immobilized thereon at least one polypeptide-cleavage reagent, especially a modified PVDF or polyethersulfone membrane having a protease, especially trypsin, covalently bonded thereto.

The invention may further be embodied as a kit for use in the method of the invention, which kit includes:

a) at least one hydrophilic membrane on which is immobilized at least one reagent capable of cleaving a polypeptide, the cleavage agent having sufficiently high activity to permit passage of the polypeptide to be cleaved and peptide fragments produced therefrom in one pass through the hydrophilic membrane, and b) a composite capture membrane suitable for receiving and capturing thereon fragments of polypeptide transferred thereto by electroblotting, the composite capture membrane being chemically modified so that captured fragments are concentrated on its surface.

The term "kit" as used herein includes combinations of the identified components in separate containers or in one container and also an assembly of the hydrophilic membrane(s) and chemically modified composite capture membrane ready for use. The kit may further include reagents useful in the method of the invention, e.g., isotopically distinct labeling reagents for quantification, electroblotting buffer, and reagent(s) which assist in the reaction of the enzyme with the polypeptide fragment.

The term "capture membrane" as used herein has a broad meaning, since this is particularly important to the performance of the invention. The membrane may be self-supporting or non-self-supporting and can be a porous membrane, film, coating or plate. The membrane will normally be porous to the electroblotting buffer to enable current to be carried to or from the electrode, but may alternatively be the electrode or in direct electrical communication with the electrode.

The term "identifying" as used herein is not to be construed as being synonymous with determining the sequence and includes partially identifying the polypeptide or characterizing the polypeptide as similar to or different from a known protein. Further, the term includes making a tentative identification based on the most probable of a small number of possibilities. Sequence can be determined by tandem MS-MS methods for the identification of unknown proteins or confirmation of known proteins.

One embodiment of the invention relates to identifying and quantifying polypeptides that have already been separated by gel electrophoresis or identifying proteins extracted from a one or two-dimensional protein array, for example, a tissue or tissue slice, by electroblotting. The nature, or the source, of the polypeptides to be identified is not critical. They can be, for example, naturally occurring proteins, proteins made by recombinant DNA technology, or polypeptides made by peptide synthesis or large peptides derived from partial cleavage of polypeptides. For brevity, the invention will be described hereinafter with reference to proteins. The extrapolation to other polypeptides will be taken as understood and incorporated throughout the following description.

The composition of gel on which the proteins have been separated is not critical, but will usually be a polyacrylamide gel. Any of the conventional gels and separation conditions may be employed, including reducing and non-denaturing conditions. They may be one-dimensional or two-dimensional gels. (In 2D gels, proteins are separated in one dimension by their charge and in the other dimension by their molecular mass). Other suitable separation modes include capillary electrophoresis, capillary electrochromatography, dynamic field gradient focusing, isoelectric focusing, liquid chromatography including affinity chromatography, thin layer chromatography, and electrophoresis using agarose gels, or starch gels.

The invention can be utilized with one or more proteins co-present on the gel, for example from 1 to 3000, and preferably 1 to 200 proteins. This includes proteins present at different molecular weight separations on a 1D gel or at similar molecular weights but present in parallel lanes or tracks on the 1D gel, as well as those separated by 2D gel electrophoresis. Normally, the electroblotting takes place overall in the direction of cathode to anode, as most of the proteins are negatively charged at the pH used in electroblotting. In order to further assure that the polypeptides and their fragments migrate toward the anode, a small amount of an additive which imparts a negative charge to the peptide such as SDS or the like may be added to the transfer buffers. The concentration must not significantly interfere with binding of the peptides to the membrane or with the activity of the immobilized cleaving reagent (e.g., trypsin), but yet it must be in sufficient concentration to interact with the polypeptides and their fragments to impart a net negative charge. The preferred concentration is usually between about 0.001 and about 0.1% w/v, and preferably between 0.005 and about 0.02%, most preferably 0.01% w/v. Depending on the pH of the electroblotting buffer used, positively and negatively charged fragments could be obtained and migrate in opposite directions, towards the cathode and anode respectively.

Figure 2A:
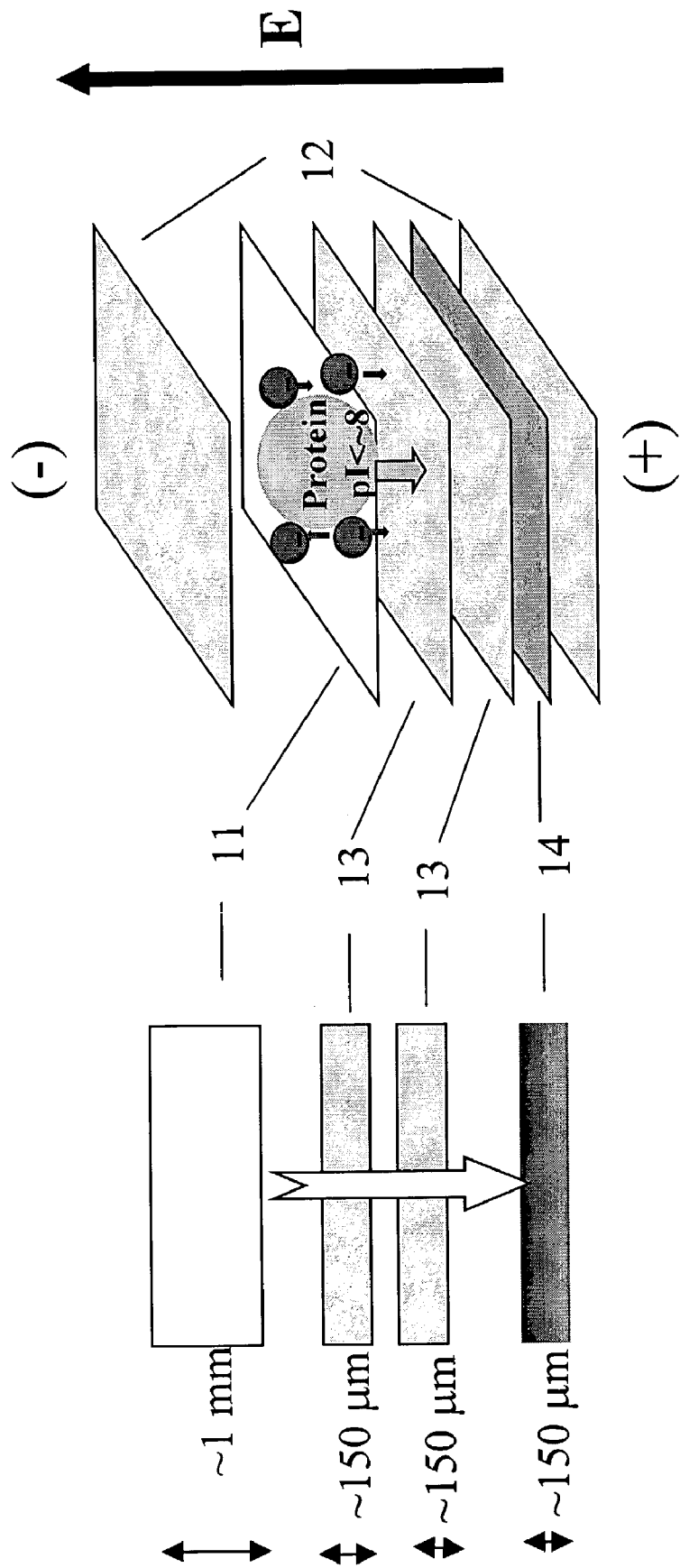
FIGS. 2a and 2b are schematic views of other embodiments of blotting "sandwich" which can be used in the invention.
Figure 2B:
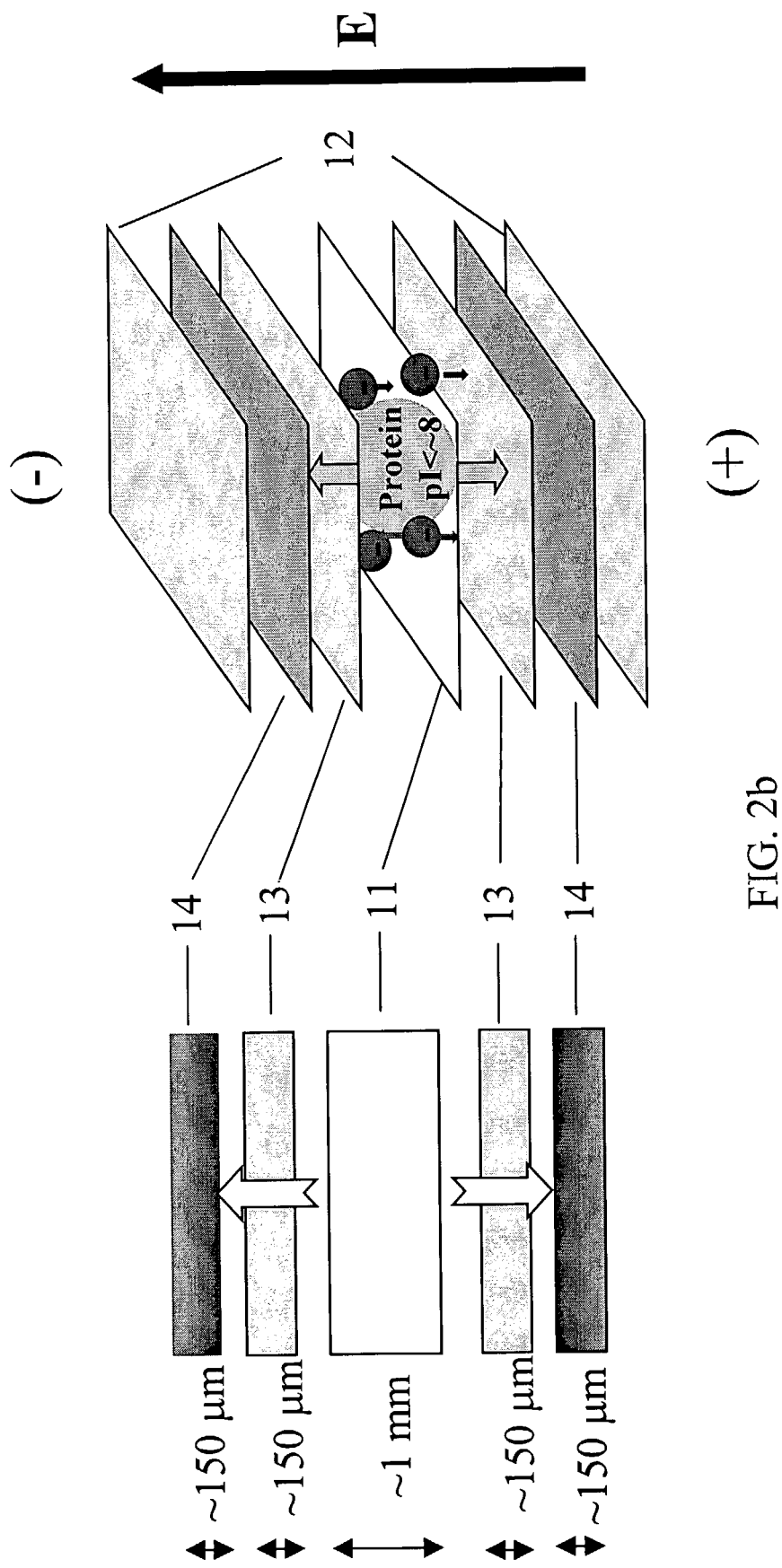

FIGS. 1, 2a and 2b exemplify some sandwich constructions useful for the electroblotting. FIG. 1 shows an experimental arrangement in which an anodic collection layer is preferably a composite capture membrane 14 having a multi-modal capture mechanism. It will be understood that under different pH conditions, some polypeptide fragments could migrate towards a cathodic collection layer. Thus, the invention includes the possibility of providing anodic and cathodic collection layers, with one or more hydrophilic membranes 13 interposed between each of them and a separation gel 11 (FIG. 2b). In FIG. 1 there is at least a single hydrophilic membrane 13, preferably a modified polyethersulfone membrane, having an appropriate protein-cleavage reagent, such as cyanogen bromide, 3-bromo-3-methyl-2-(2-nitrophenylmercapto)-3H-indole (BNPS-skatole) or the like, preferably a protease enzyme, for example trypsin, immobilized on it, interposed between the gel 11 and the anodic composite capture membrane 14, which can be formed from materials such as PVDF, Nylon or nitrocellulose, and which is most preferably a chemically modified PVDF composite capture membrane, on which the protein fragments are collected. In FIG. 2a. there are two consecutive hydrophilic membranes 13, preferably modified polyethersulfone membranes, each with trypsin immobilized thereon, placed between the gel 11 and the anodic collection layer, which, again, is preferably a chemically modified PVDF composite capture membrane. FIG. 2b. shows a similar arrangement in which there are digestion membranes 13 on both sides of the gel 11, and both an anodic and a cathodic capture membrane.

In more detail, the anode and cathode are separated from the rest of the sandwich by an absorptive layer 12 that is soaked with the blotting liquid, while maintaining the liquid in electrical contact with the electrodes, and is preferably a filter paper. The kinds of electrodes and absorptive layers used in arrangement are not critical and can be any type conventionally used in electroblotting.

The "filling" of the sandwich can take the form of one or more membranes 13 (defined as shown in FIG. 2a) sufficiently hydrophilic in character such that the proteins and fragments thereof do not tend to stick on the membrane. This membrane can be any layer which is porous to the electroblotting liquid and capable of immobilizing the polypeptide-cleavage reagent thereon, whether on the surface thereof or within the interstices or microcavities therein that are accessible to the electroblotting liquid (and therefore to the polypeptide to be cleaved). The membrane is typically from 100 to 600 micrometers thick; for example, a Gelman US450 membrane (Pall Life Sciences) is about 150 micrometers thick. Usually the number of such membranes included in the sandwich will be from 1 to 7. With conventional thicknesses of membrane, 4 membranes will frequently be used. They are best placed directly and mutually adjacent, i.e., one on top of another. The hydrophilic membrane(s) are preferably provided with "active carbonyl" or carboxylic acid groups or derivatives thereof reactive with amino groups present in enzymes. "Active carbonyl"-modified or carboxyl-modified PVDF membranes or polyethersulfone with aldehyde activation membranes are especially preferred.

An aldehyde activated membrane is used to immobilize polypeptide cleavage reagent such as a protease. To enhance cleavage activity, a method is described that increases the amount of active proteolytic enzyme to be immobilized on the hydrophilic membrane. The immobilization conditions include the addition of salts such as sodium sulfate or the like at concentrations between about 0.1 and about 1.5 M, preferably between about 1.1 and about 1.5 M and a protease inhibitor such as benzamidine or the like (in the case for trypsin) to the reaction mixture to ensure active enzyme is immobilized to the membrane. The Schiff base formed during this reaction is then reduced with sodium cyanoborohydride (or other suitable reducing agent) to produce covalent irreversible attachment. The protease inhibitor then is removed from the membrane such as with 1 M sodium chloride so that the immobilized cleavage reagent is free to digest the polypeptide to form peptide fragments.

Because it would be difficult to react all the active groups present on the surface of a membrane with an enzyme, and because it is undesirable to allow the polypeptides to react with these free active groups, the residual active groups (which would otherwise be free) are preferably capped before the membrane is used, e.g., with ethanolamine, or for aldehyde activated membranes, with Tris(hydroxymethyl)-aminomethane (Tris) and sodium cyanoborohydride, thus providing terminations such as ——CO——NH——$CH_2$——$CH_2$——OH, which are relatively hydrophilic. Other conventional hydrophilic capping groups can be utilized. Alternatively, PVDF membranes or glass fiber paper can be functionalized by isothiocyanate, which allows reaction with the epsilon-amino groups of lysine residues in the enzymes. For this purpose, the PVDF membranes are pre-treated with NaOH to provide a carbon-carbon ethylenic double bond in the polymer chain (by elimination of a molecule of HF). The pre-treated PVDF membranes are then reacted under basic conditions with a dinucleophile such as ethylenediamine, 1,10-diaminodecane or 2-aminoethanethiol, whereby hydrogen atoms in the polymer are substituted by ——X——$(CH_2)_n$—$NH_2$ groups, wherein X is ——S—— or ——NH—— and n is from 2 to 10. This polymer, having amine-terminated side-chains, is then reacted with 1,4-phenylenediisothiocyanate (DITC) or 3,5-dichloro-1,4-phenylenediisocyanate (DCDITC) to give the required isothiocyanate-terminated side-chains in good yield. DITC-reacted glass fiber sheets provide another form of membrane.

Another form of membrane is PVDF functionalized by arylamine groups, which react with a carboxylic acid sidechain or the carboxyl terminus of the enzyme, preferably in the presence of a carbodiimide such as 1-(3-dimethylaminopropyl)-3-ethylcarbodiimide. Another form of hydrophilic membrane that can be used as the sandwich filling is a thin film or coating of agarose gel. The epsilon-amino groups of lysine residues in the enzyme are treated to obtain aminoxy groups, which react with aldehyde groups produced by mild oxidation of the agarose gel, thus bonding the enzyme covalently to the agarose.

The cleavage reagent is normally and preferably immobilized by covalent bonding in the presence of one enzyme inhibitor that is subsequently removed. However, other forms of immobilization are not excluded from use in this invention, so long as the enzyme does not become sufficiently free in solution in the electroblotting liquid as to undergo autodigestion. (It will be understood that the presence of auto-digested enzyme fragments could interfere with the analysis of the fragments from the protein to be analyzed). Thus, for example, the enzyme could be physically trapped within the pores of a porous sheet of hydrophilic polymer. Alternatively, the membrane could have an enzyme immobilized thereon by means comprising affinity bonding. Thus, the enzyme could be covalently attached to avidin or streptavidin and the resultant conjugate attached to a biotinylated membrane by affinity bonding between avidin/streptavidin and biotin. Alternatively, avidin or streptavidin could be attached to the membrane and the enzyme could be reacted to provide biotinyl terminations for reaction with a membrane to which avidin or streptavidin has been attached.

Preferably the cleavage agent is an enzyme and most preferably and usually one which cleaves the main chain of the polypeptide, especially trypsin. Trypsin cuts proteins at the carboxyl side of lysines and arginines. Other less specific endoproteases, e.g., pepsin or chymotrypsin are usable, as are the highly specific enzymes Lys-C, Arg-C or Glu-C. For phosphoproteins, a phosphatase may be useful, either alone or in combination with proteases, thus enzymes may include those that react with protein side-chains. More than one enzyme can be immobilized on the membrane. For example, it may be helpful to carry out partial cleavage from the polypeptide termini, e.g., using a carboxypeptidase or aminopeptidase in conjunction with an endoproteinase. Carboxypeptidase Y is one particularly useful such enzyme.

The concentration of cleavage reagent immobilized on the digestion membrane in accordance with the present invention is sufficiently high such that after a single pass of the sample through the membrane, all or substantially all of the protein in the sample is digested and the sample is devoid or substantially devoid of undigested protein. In an attempt to estimate the degree of digestion, an *E.coli* lysate was separated on a preparative gel. Using a Bio-Rad mini whole gel eluter, the separated lysate was electroblotted from the separation gel and collected in fraction tubes. The fractions were then subjected to 1D gel separation followed by Coomassie staining, showing a "molecular weight ladder" of the separated fractions. Since the mini whole gel eluter employs electroelution, a second experiment was performed where a membrane containing the immobilized cleaving reagent was placed between the separation gel and the collection reservoirs. Single fractions from both experiments were compared by subjecting each of the fractions to 1D gel analysis. The expectation was that if there was insufficient digestion in the experiment where the cleaving membrane was used, intact protein would be observed in the second 1D gel analysis. The fraction obtained from the experiment without the cleavage membrane was serially diluted to get a relative estimate of how much intact protein remained in the 1D gel comparison. For this experiment, instead of staining with Coomassie, the more sensitive Sypro Ruby fluorescent stain was used. It was found that the amount of protein remaining in the fraction exposed to the cleaving membrane was less than the highest diluted fraction from the experiment that did not use the cleaving membrane. It was estimated that greater than 95% of the protein was digested in the single pass through the immobilized trypsin membrane.

In addition, previously oscillating current was necessary in order to afford sufficient residence time of the sample contacting the cleaving reagent to effect adequate and effective digestion. In view of the increased cleavage reagent concentration on the digestion membrane in accordance with the present invention, oscillating current is no longer necessary. Although quantitative measurements of cleavage reagent concentration immobilized on the membrane are difficult and can vary depending upon the measurement method used, levels of trypsin in the range of about 20 μg/cm$^2$, as measured by the BAPNA assay, are achievable, compared to conventional levels as high as only about 8 μg/cm$^2$. These relatively high levels of cleaving reagent in accordance with the present invention have resulted in a significant increase in effectiveness of the digestion process.

To investigate the presence of certain protein chemical modifications, such as carbohydrates containing glucosyl, N-acetylglucosaminyl and sialyl groups, enzymes which will cleave those chains, such as glucosidase, N-acetylglucosaminidase and neuraminidase, respectively, are useful in the invention, especially in combination with proteases. In such cases, it may be desirable to analyze samples using proteases alone, and separately in combination with these additional enzymes.

The cleavage reagents are not confined to enzymes, but could include chemical reagents, for example, cyanogen bromide, which could be physically immobilized by entrapment within a porous matrix.

The anodic composite capture membrane 14 (and cathodic collection layer composite capture membrane, if used) can be any composite capture membrane used in electroblotting, such as PVDF, nylon or nitrocellulose or the like, with or without modifiers. The modifiers may include any chemicals that do not interfere with subsequent mass spectrometry analysis, for example, polymers or moieties that interact with either the carboxyl or amino moiety to immobilize the peptide fragment on the composite capture membrane surface.

A preferred capture membrane is a composite membrane made from PVDF modified with a quaternary amine available from Millipore Corporation (Bedford, Mass.) as Immobilon CD. In accordance with an important aspect of the present invention, this membrane is preferably modified with nitrocellulose and HCCA to create a hybrid membrane with multiple peptide interaction modes that capture and promote ionization of the peptide fragments when exposed to laser desorption such as by a MALDI ionization process.

Figure 3A:
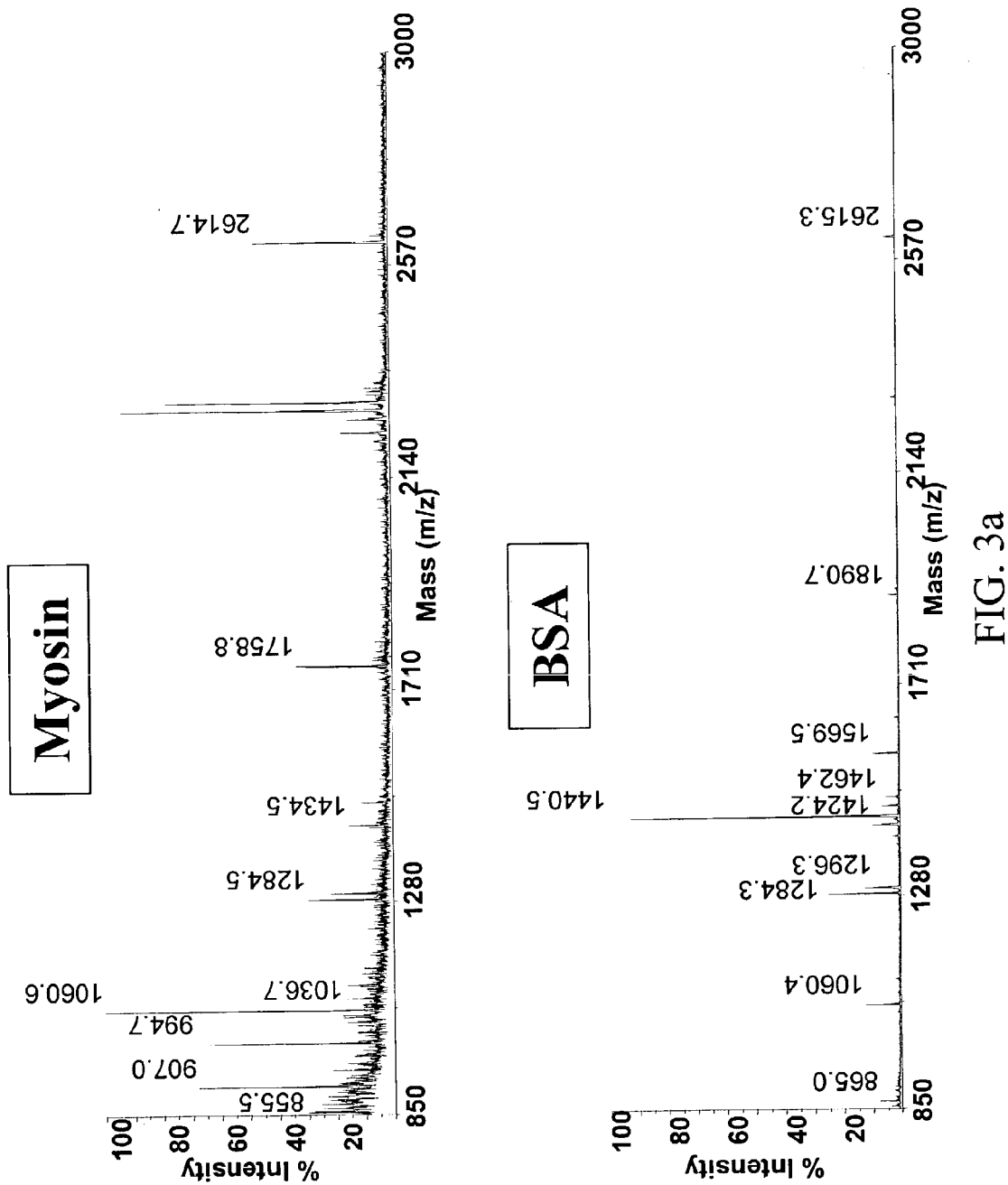
FIGS. 3a and 3b show the MALDI-TOF MS spectra obtained from four different standard proteins, i.e., myosin, BSA, ovalbumin, and carbonic anhydrase.
Figure 3B:
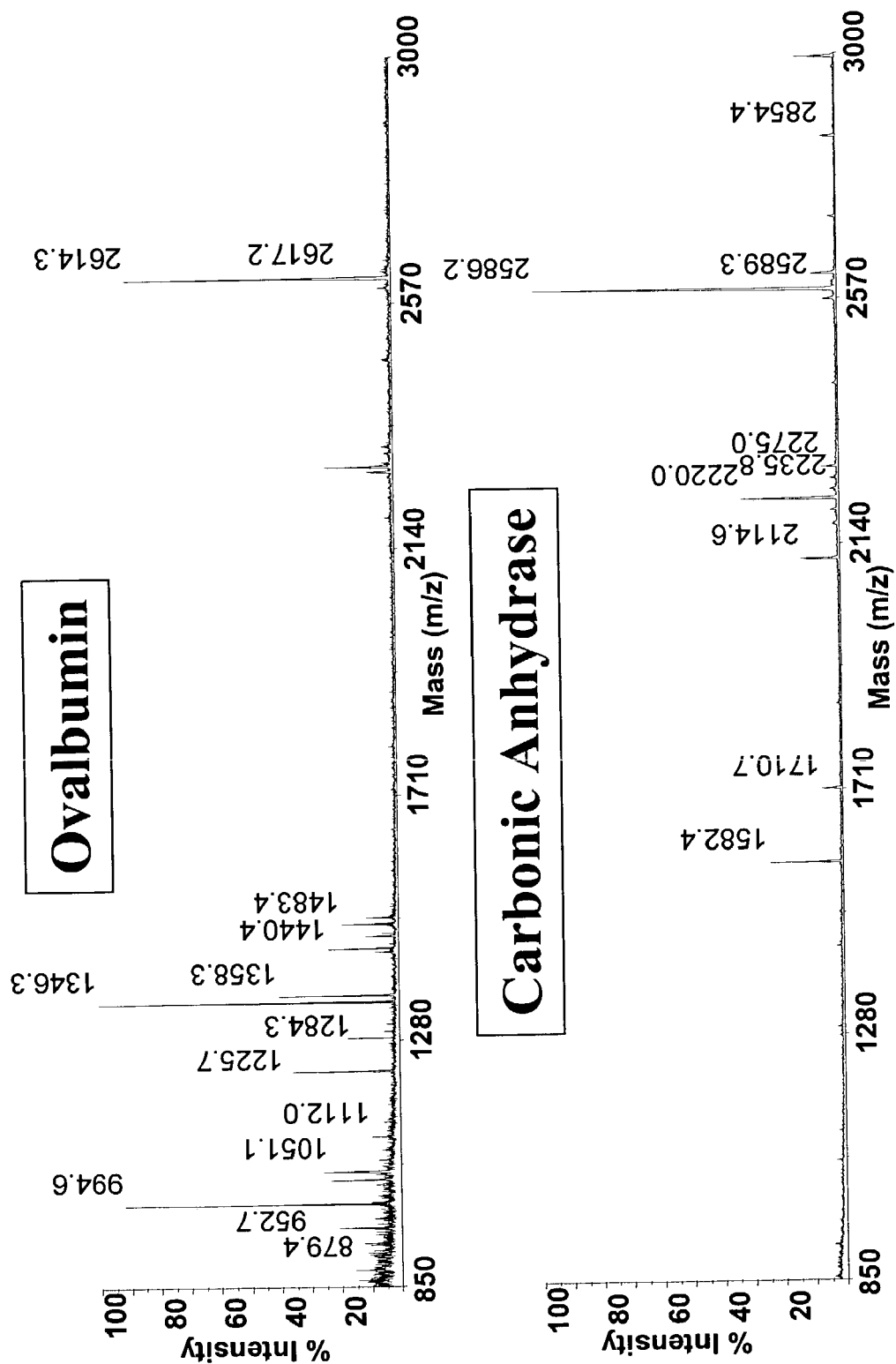
Figure 4:
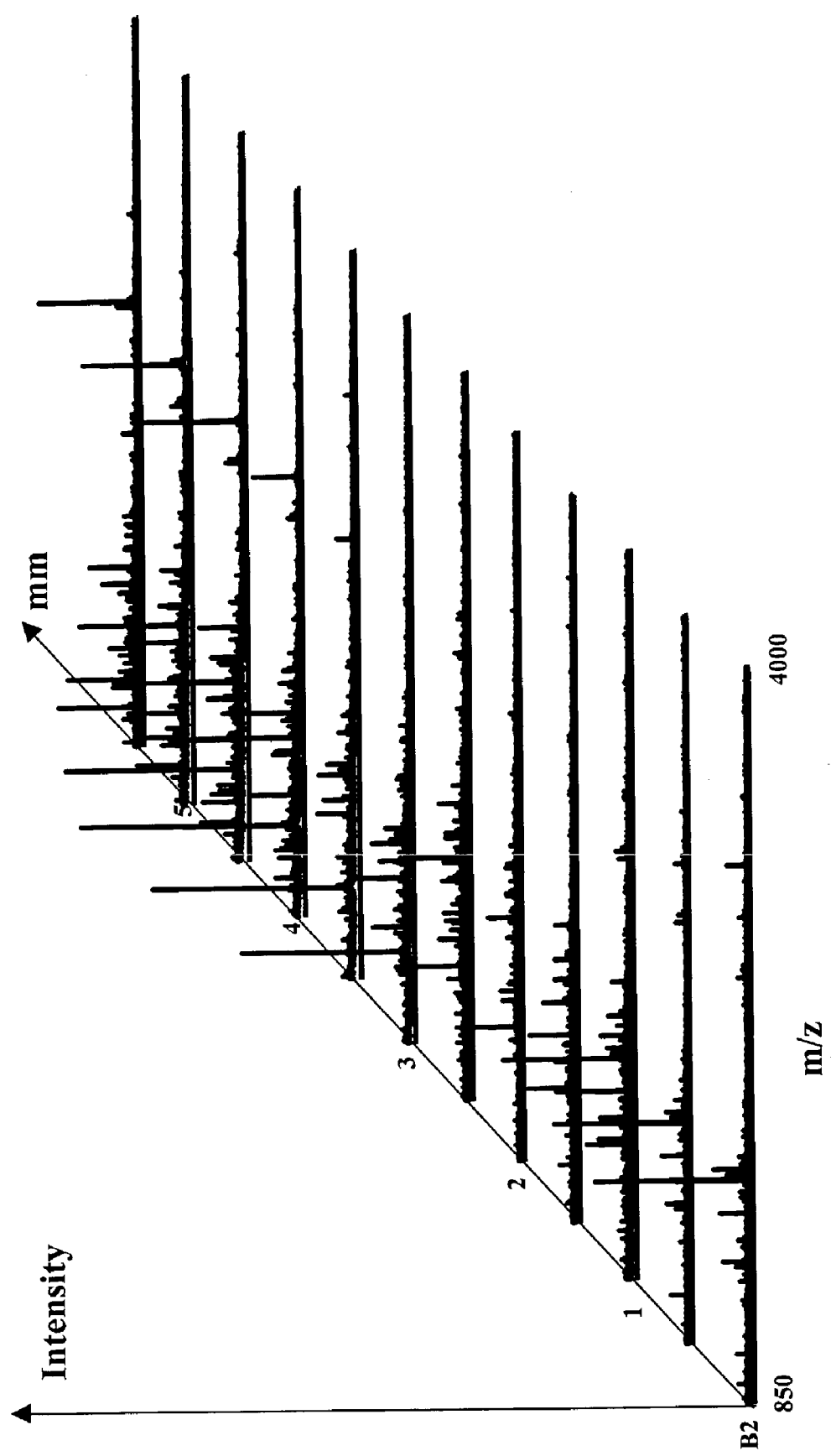
FIG. 4 shows 12 MALDI spectra obtained from consecutive locations of a 1D SDS_PAGE minigel of an *E. coli* lysate. Each spectrum was separated by 500 microns.

In a preferred embodiment, the capture membrane 14 is treated in advance with a mixture of nitrocellulose and HCCA, dissolved in acetone. This has the effect of creating a more efficient capture substrate for the newly formed peptides, thereby greatly increasing the sensitivity and robustness of subsequent MS detection. Representative mass spectra obtained from some molecular weight standard proteins are shown in FIGS. 3a and 3b. Each of these proteins was automatically identified using the Protein Prospector data base search program (University of California, San Francisco). In FIG. 4, an E. coli lysate was loaded onto a SDS-PAGE minigel, and spectra were acquired every 0.5 mm down the gel. Twelve consecutive spectra are shown. One can see that many peptides are detectable in several adjacent slices. The typical pattern is that each mass is strongest in one slice, and then is detectable, but weaker, in the adjacent slices. This is exactly the kind of distribution one would expect from a sample that had many hundreds of proteins-; each protein would produce a distribution of peptides that would have approximately a Gaussian distribution of intensity vs. distance, and the overall mass spectra would consist of the sums of these Gaussian distributions. We have been able to identify with confidence more than 4 proteins from individual spectra using software as described in a co-pending U.S. patent application Ser. No. 09/745,920, herein incorporated by reference and commonly assigned, that is designed specifically to deconvolute the peptide mass fingerprints of multiple protein components.

Stable isotope labeled reagents for the purpose of tagging two different preparations of proteins, e.g., from two different protein fractionations, proteins isolated from cells from normal vs diseased tissue, proteins isolated from mutant cells vs. wild-type cells etc., can be used together with the kit of this invention to obtain quantitative information. This methodology has been described in published PCT Patent Application WO 00/11208 whose disclosure is incorporated by reference herein. ICAT™ reagents commercially available from Applied Biosystems are an example of such isotope-labeled reagents that can be used to differentially label proteins. In addition, the relative quantification of expressed proteins separated on 1D gels using ICAT reagents has also been demonstrated as described in published PCT patent application WO 02090929. The typical procedure of gel-cutting, in-gel digestion and peptide mass fingerprinting was used to identify and quantify the proteins in the gel slices. Other isotope-labeling reagents include reagents that react with other amino acid side-chains, for example amino groups or carboxylic acid groups. For example, esters of N-hydroxysuccinamide, where the ester group contains any combination of stable isotopes of hydrogen, carbon, nitrogen, oxygen, sulfur, halogen, react with amino groups thereby labeling the protein with a moiety containing the stable isotope label that is distinguishable by mass spectrometry. Because these stable isotopes have little effect on the intensities measured by mass spectrometers, the ratio of the light and the heavy form of the peptides indicates the relative abundance of the protein from which that peptide was derived in the two starting samples. For example, comparisons of protein expression profiles of normal and malignant cells can result in the identification of proteins whose presence or absence is characteristic and diagnostic of the malignancy.

Figure 5:
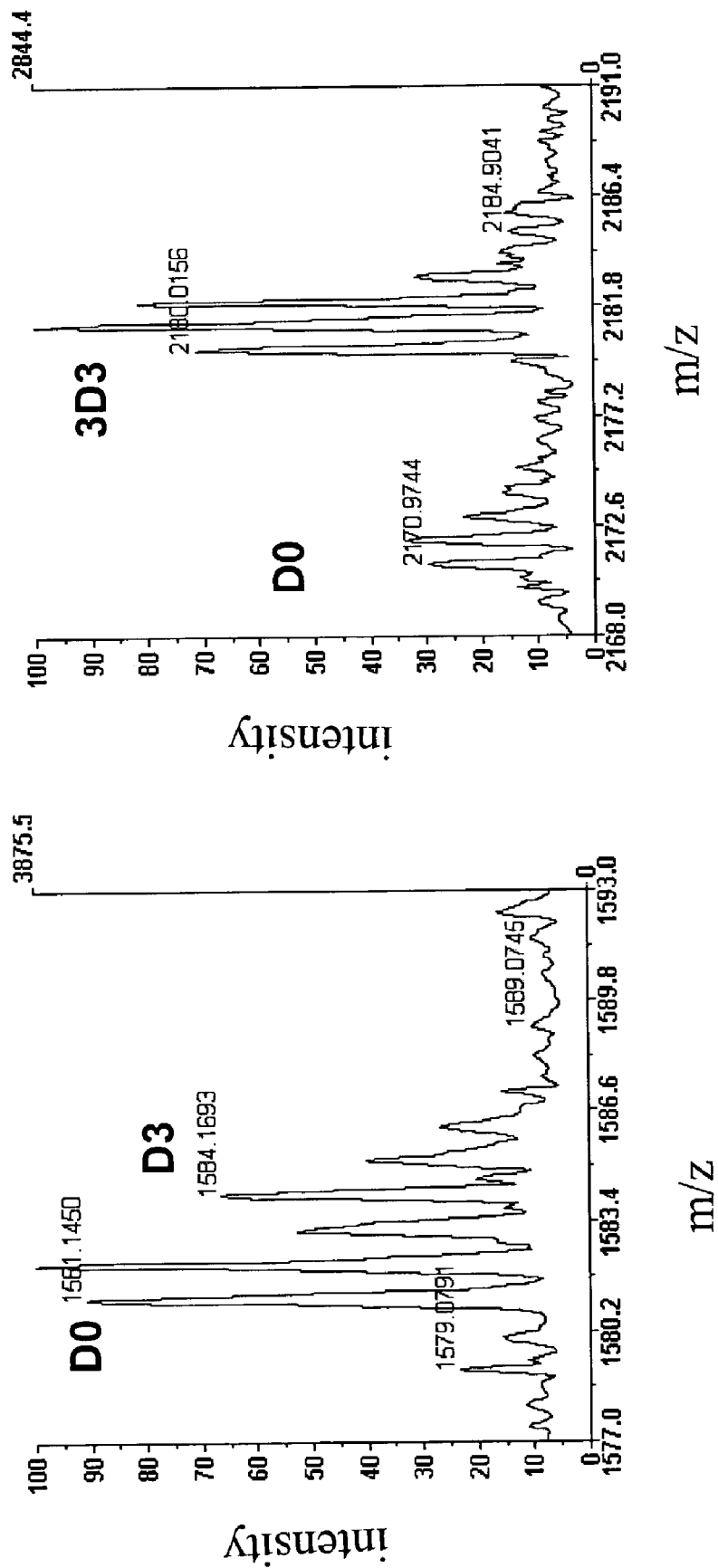
FIG. 5 shows two different examples of MALDI-TOF MS spectra of peptide pairs that can be used for isotope labeled protein quantification. The left panel of FIG. 5 shows a peptide pair containing one acetylated lysine residue from a protein (trypsin inhibitor) that was mixed at a 2:1 ratio after being labeled separately with the hydrogen form of acetate, and the deuterated form of acetate. In the right panel of FIG. 5, another peptide containing three acetylated lysine residues from the same protein (trypsin inhibitor), separately labeled with the hydrogen form of acetate and the deuterated form of acetate, was mixed at a 1:3 ratio.

In FIG. 5, small regions of two different MALDI-TOF spectra are shown in which there are pairs of peptides. In these experiments, the protein trypsin inhibitor was labeled with either non-deuterated NHSA or tri-deuterated NHSA, mixed in either a 2:1 or 1:3 ratio and treated with the method and apparatus described in this invention. The peptides derived from this experiment were analyzed using a MALDI-TOF mass spectrometer and the ratios of the intensities of the peptides with and without the heavy isotopes were measured and compared to the original starting mixture. In the left panel, the samples of trypsin inhibitor were mixed at a 2:1 ratio prior to separation by gel electrophoresis and electroblotting through the digestion membrane. The capture membrane 14 containing the mixture of heavy and light forms of the peptides were subjected to MS analysis. The right panel is from a different experiment in which the samples of trypsin inhibitor were mixed at a 1:3 ratio and subjected to the same process as described above. In the left panel, the peptide displayed contains a single lysine residue, and therefore 3 mass units separate the two peptides from one another. Due to natural occurrence of C-13 and other heavy isotopes, the mass at 1581 (peptide with light isotope) is partially overlapping the mass envelop of the peptide containing the heavy isotope, as shown. The peptide in the right panel has 3 lysine residues. All three lysines have become acetylated causing the modified peptide pair to be separated by 9 mass units (3 deuterium atoms×3 lysines residues), which even at a mass of 2170 is sufficient such that the isotope envelope for each form of the peptide are completely non-overlapping. Because all of the lysine residues in the original protein have been acetylated, trypsin cleaves the protein only at arginine residues, which decreases the number of fragments that can be generated from each protein using the most reliable endoproteinase, trypsin, and increases the molecular weight of many of the peptides. This makes it possible to detect a larger percentage of the primary structure of each protein by mass spectrometry.

Figure 6A:
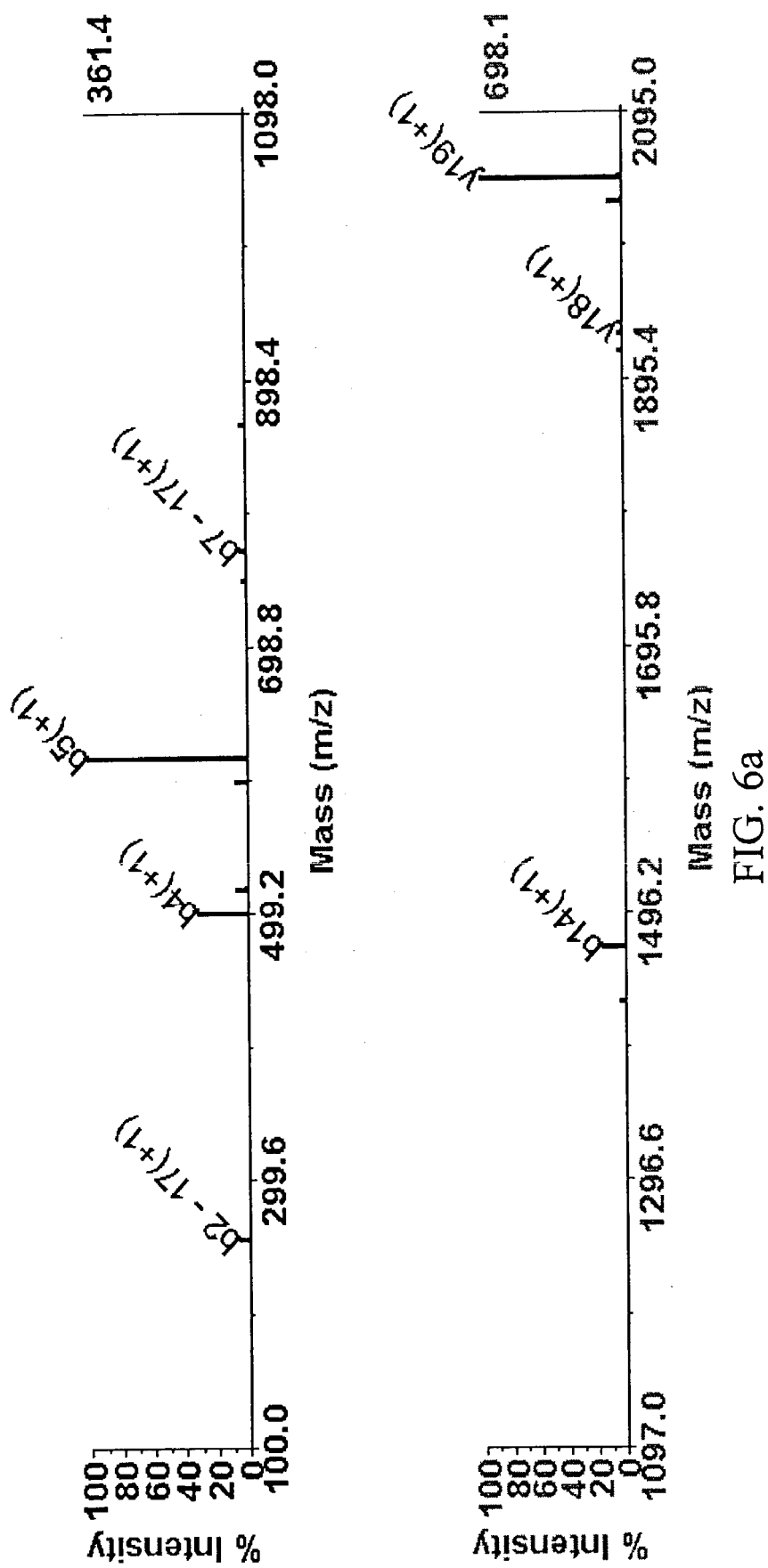
FIG. 6a shows an orthogonal (o)-MALDI-MS-MS spectrum of an *E. coli* peptide from 30S ribosomal protein (Swiss Prot accession #P02349).
Figure 6B:
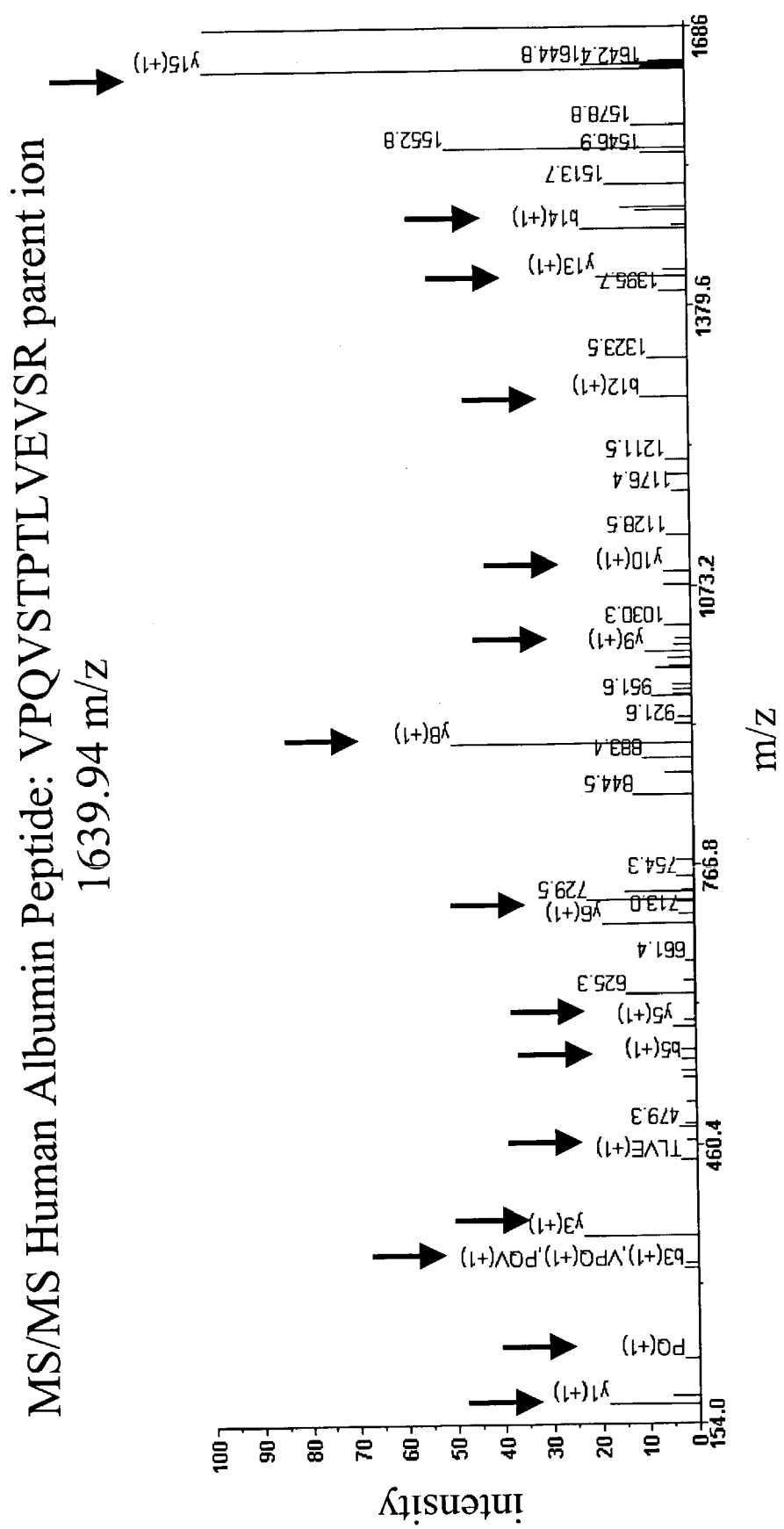
FIG. 6b shows a MALDI-TOF MS-MS spectrum obtained from a peptide ion (1639.94 m/z) derived from human serum albumin separated from serum by 1D gel electrophoresis.

In FIG. 6a, a MS-MS spectrum that was acquired using a QSTAR® MS system with oMALDI ion source (Applied Biosystems) is shown for one of the tryptic peptides derived from a protein in an E. coli lysate separated using a ID gel. The spectrum in question was matched to E. coli 30S ribosomal protein S1 peptide DRVEDATLVLSVGDE-VEAK using the MS-Tag routine of the Protein Prospector Program. In FIG. 6b the MS-MS spectrum of a peptide ion derived from a serum protein separated on a 1D gel was acquired using a tandem time of flight MALDI MS, the 4700 Protein Analyzer with TOF-TOF™ Optics (Applied Biosystems), is shown. The spectrum was matched to human serum albumin peptide VPQVSTPTLVEVSR.

In contrast to U.S. Pat. No. 6,221,626 and published PCT patent application WO 00/45168, improvements in immobilizing the enzymes to the digestion membrane promote cleavage activity, and thus there is no need for a pulsed or alternating current generator. The electrical current applied in the electroblotting is thus preferably a direct, continuous current. Alternatively, a pulsed current, i.e., a direct current with intervals in which no current is passed, or an alternating current biased in the cathode to anode direction, i.e., mainly a cathode to anode current, but with intervals in which current is passed in the opposite direction can also be used. Variations on these regimes are possible within the general spirit of the idea of performing a slower than normal electroblotting, allowing time for the cleavage to take place on the hydrophilic membrane(s), while not causing so much delay in the travel of the proteins and fragments from the separation gel to the collection membrane that would cause undue lateral (sideways) diffusion, causing loss of resolution. It is preferred to utilize a pulsed or continuous direct current since the time for the peptide to migrate to the composite capture membrane is substantially reduced, and the equipment to accomplish this is widely available.

The electroblotting liquid is preferably a buffered solution containing a detergent and can be any conventional buffer for this purpose, such as Tris/glycine with methanol, SDS or 3-(cyclohexylamino)-1-propanesulfonic acid (CAPS) with methanol. The direction of migration of the fragments depends essentially on the pH of the buffer and detergent concentration. For most purposes an alkaline buffer will be appropriate, since many hydrolytic enzymes function best at alkaline pH. Some enzymes, however, such as pepsin, require an acidic pH. Under such conditions, the fragments will migrate to the cathode and a cationic detergent such as CTAB (cetyl trimethylammonium bromide) is preferred.

Peptides derived from the main chain of the protein are collected on the capture membrane. They are then preferably analyzed by MALDI-TOF MS or tandem MS/MS in a conventional way. Examples of such MS techniques are described in U.S. Pat. Nos. RE 37485; 5,760,393, and 6,348,688, each of whose disclosure is incorporated herein by reference. This analysis may involve an additional step of treating the membrane a second time with matrix. The sample is excited by UV, or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very sensitive. MALDI mass spectrometers suitable for this analysis are commercially available from Applied Biosystems (Foster City, Calif.).

In this invention, the above described method is applied to the scanning of the fragments of many proteins at once. Thus, many proteins can be run simultaneously by PAGE, subjected to the method of the invention to produce an array of spots on the collecting membrane and the array analyzed as follows. The composite capture membrane is cut and fixed on the MALDI-TOF MS sample plate with silicone grease, conductive tape, double sided tape or a curing glue. An organic matrix-forming reagent is added to the membrane on the sample plate and the sample is then air-dried. The sample plate is inserted in the MALDI-TOF MS or tandem MS/MS instrument. An automated movement of the sample plate from a first to a second position is arranged by computer program. At each position a MALDI-TOF MS spectrum is generated, the spectral information collected in digital form and the data or mass list of peptides observed downloaded to a search algorithm for peptide matching. In tandem MS/MS mass spectrometers, peptide sequence data are derived by collision induced dissociation of the peptide ion to form peptide ion fragments whose masses are observed in a second mass analyzer.

It is then simple to obtain automated output of the results listing which proteins have been identified by using software supplied by the MS instrument vendors and commercially available database search engines. One commercially available program is Protein Prospector previously discussed.

It is evident, therefore, that the present invention has huge potential for the automated identification and/or partial characterization of many proteins simultaneously. In effect, the invention provides in this preferred embodiment a practical "molecular scanner" that will be useful for routine biochemical analyses.

Figure 7:
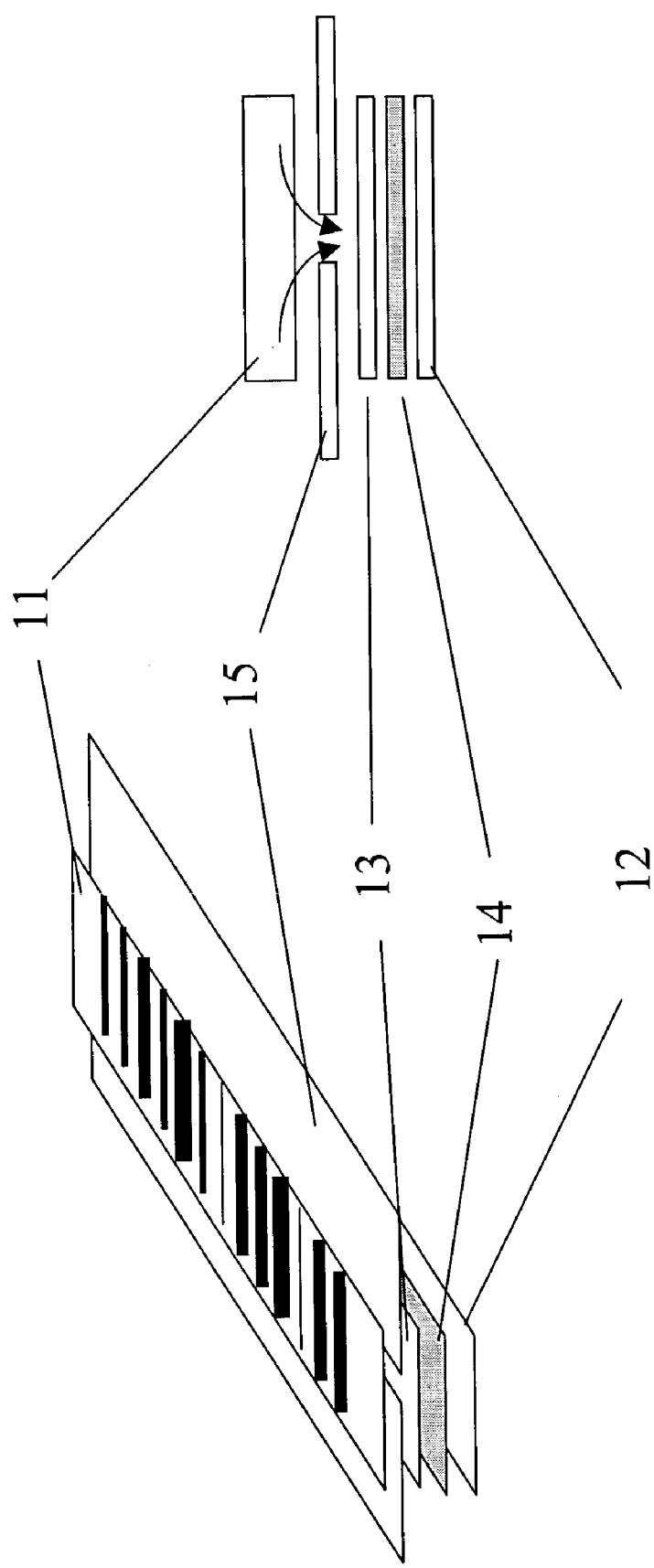
FIG. 7 is a schematic view of another embodiment useful for focusing digested polypeptides onto a discrete zone on the capture membrane.

When the mass spectrometer is used to acquire images of electroblotted proteins, it is to be expected that large surfaces of the capture membrane may be blank, because few polypeptides were present at the corresponding region of the gel that was electroblotted. To save time at the level of data acquisition, and to increase sensitivity, FIG. 7 shows another embodiment useful for focusing digested polypeptides onto a discrete zone on the capture membrane. As shown, a nonconductive sheet 15 with slits or holes can be placed between the gel 11 and the capture membrane 14 to focus or restrict electro-blotting to specific regions of the capture membrane. In the case of 1D SDS-PAGE, no spatial resolution is sacrificed by this means, so long as the direction of the slit is parallel to the direction of electrophoresis. Thus, the ideal nonconductive sheet would have slits centered on each lane of the 1D gel. The corresponding device for 2D-gels would consist of a series of regularly spaced holes. This sheet would reduce the area that needed to be scanned, at the cost of some spatial resolution. The nonconductive sheet 15 could be placed either before or after the cleavage membrane 13, depending on which location was found to be most productive.

In biochemistry, the ability to quantify the differences in protein abundance between two samples is of considerable interest. In one embodiment, this invention can be utilized with analytical reagents and mass spectrometry-based methods using these reagents for the rapid, and quantitative analysis of proteins or protein function in mixtures of proteins. The analytical method can be used for qualitative and particularly for quantitative analysis of global protein expression profiles in cells and tissues, i.e., the quantitative analysis of proteomes. The method can also be employed to screen for and identify proteins whose expression level in cells, tissue or biological fluids is affected by a stimulus (e.g., administration of a drug or contact with a potentially toxic material), by a change in environment (e.g., nutrient level, temperature, passage of time) or by a change in condition or cell state (e.g., disease state, malignancy, site-direction mutation, gene knockdowns and knockouts) of the cell, tissue or organism from which the sample originated. The proteins identified in such a screen can function as markers for the changed state. For example, comparisons of protein expression profiles of normal and malignant cells can result in the identification of proteins whose presence or absence is characteristic and diagnostic of the malignancy.

Another preferred use for the invention is the analysis of proteins directly electroblotted from tissues or tissue slices. Recently, intact proteins from tissues have been analyzed by MALDI-TOF mass spectrometry by directly ablating them from tissues as disclosed in U.S. Pat. No. 5,808,300 which is incorporated herein by reference. Once ionized, the mass of the intact proteins, and in favorable instances, the masses of fragments that are randomly generated in the mass spectrometer are measured. These masses are then used to identify the protein. However, it is to be expected that in many instances such favorable fragments will not be detectable, and it will be necessary to resort to proteases to cleave the proteins to more efficiently generate peptides that can be used in the identification of the protein. In this application of the molecular scanner, proteins can be electroblotted in accordance with the present invention through the polypeptide cleaving membrane 13 to generate peptides that are then collected on the capture membrane 14 for identification purposes. As with the intact protein masses, an image of the tissue may be reconstructed based on analysis of the peptide masses derived from proteins that were electroblotted, digested and captured with the present apparatus. FIGS. 8a and 8b show images of a chicken heart slice, reconstructed based on the distribution of two arbitrary peptide ions (m/z 1253 and 2448) observed after the tissue slice was subjected to the method and apparatus described in the present invention. A total of 6561 (81×81) spectra were acquired and analyzed. The ion intensities are reflected for each of the peptide ions using a gray scale in FIGS. 8a and 8b. These preliminary results indicate that a distinct distribution of peptides 1253 and 2448 can be observed. The mass spectrometer that is employed could be a classical MALDI-TOF mass spectrometer, or it could be a tandem mass spectrometer that selects desired parent ions followed by MS-MS fragmentation.

Other samples containing proteins could also be used with the present invention. For example, colonies of bacteria or eukaryotic cells could be screened for the expression of recombinant protein by using the kit. In this embodiment, the colonies would first be blotted onto a membrane, and that membrane could be placed into the cassette in place of the polyacrylamide gel 11. Note that it is not crucial that the proteins be efficiently transferred out of the blotting membrane so long as a sufficient amount of peptides is captured. A second application could be at the level of determining the species of individual colonies of microorganisms isolated from environmental samples. All of the samples on a bacterial plate could be processed in parallel. Alternatively, colonies from a large number of plates could be transferred to a second plate to generate a 2-dimensional array of colonies. In this way, hundreds to thousands of colonies could be processed simultaneously, and the mass spectrometer could be operated to collect spectra from the known coordinates of the 2-dimensional array.

Figure 9A:
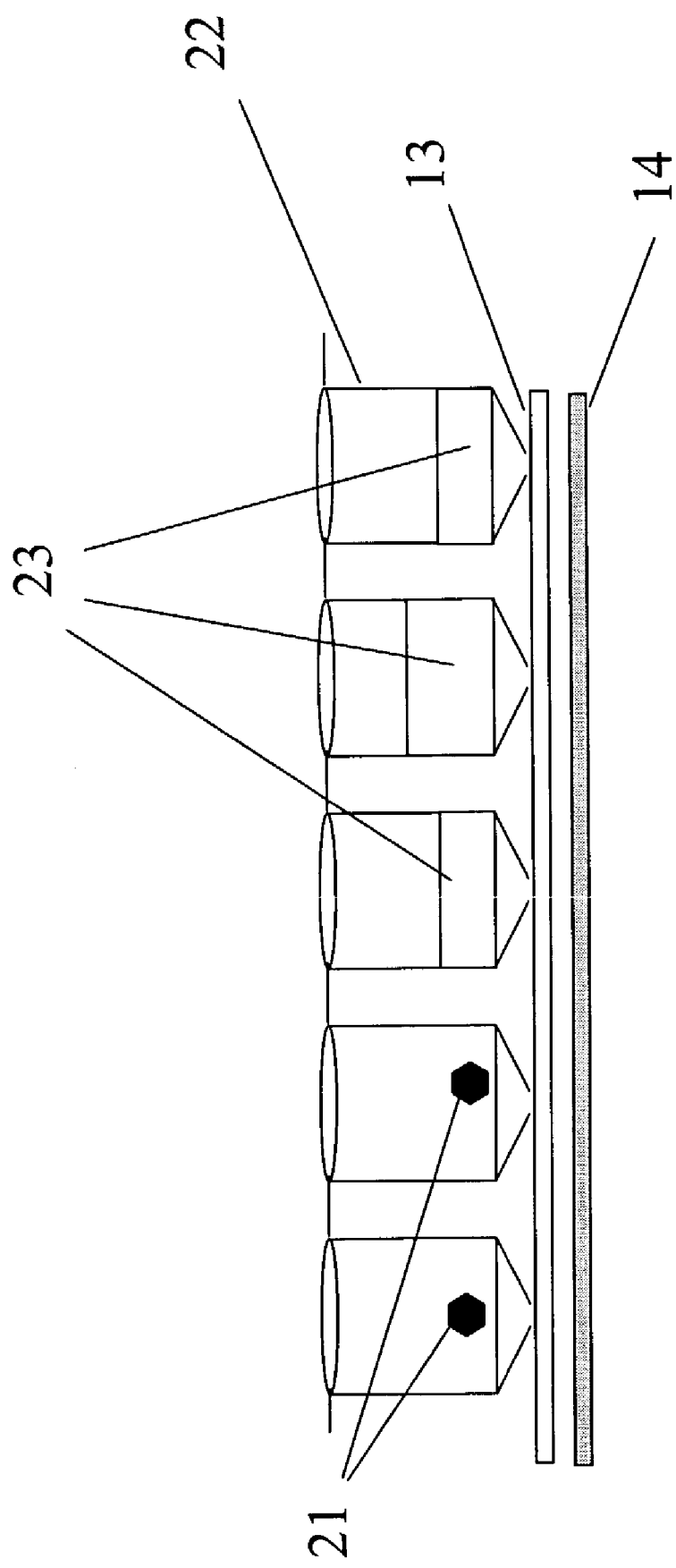
FIGS. 9a and 9b show schematic views of another embodiment useful with microtiter plates.
Figure 9B:
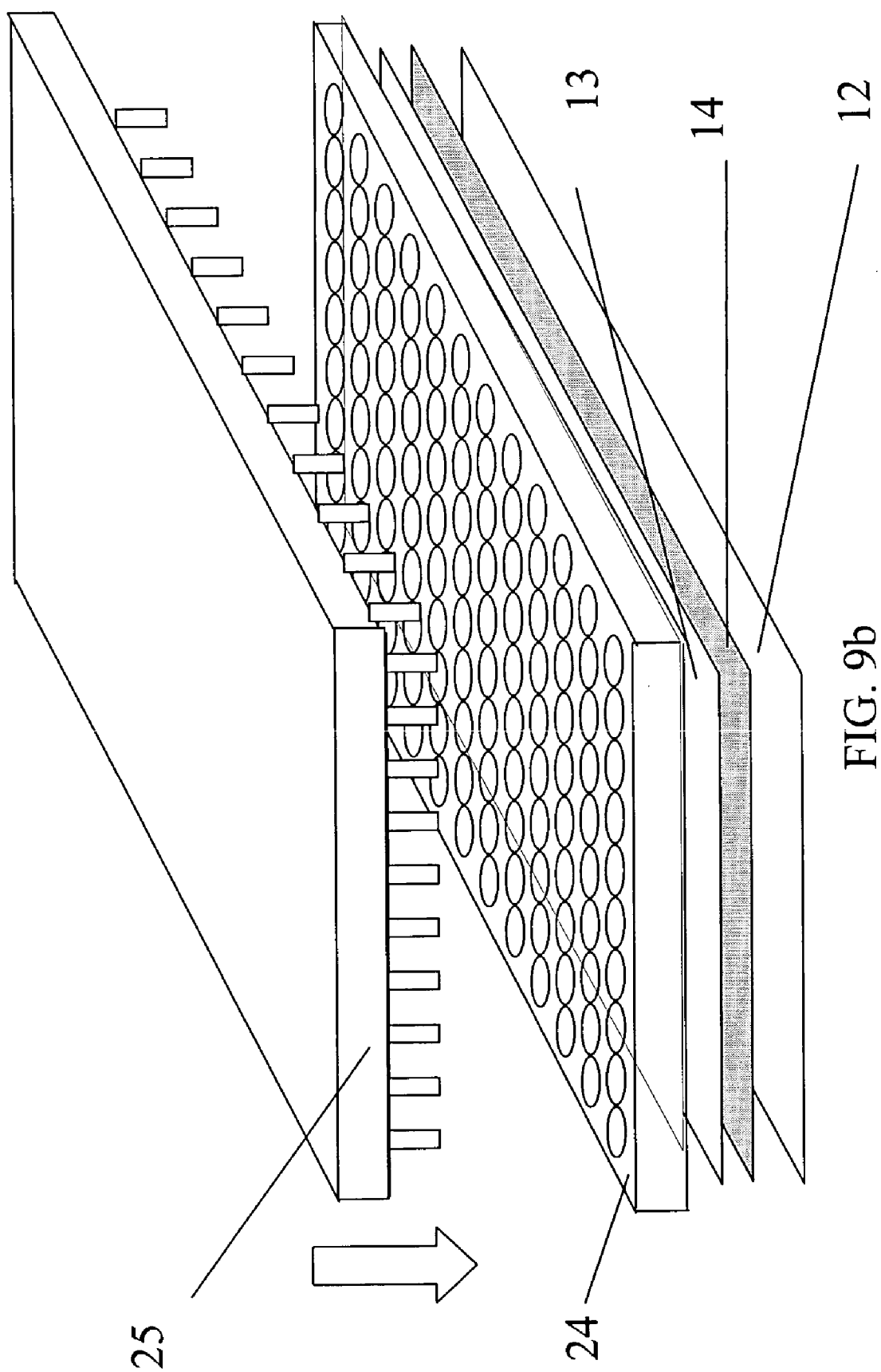

In another embodiment described with reference to FIGS. 9a and 9b, the proteins could originate in a microtiter plate 24 equipped with filters below each well 22. An electrode manifold 25 with, e.g., 96 wires could dip into each of the 96 wells from the top, as shown in FIG. 9b. So long as the wells contained a buffer that was suitable for blotting, it is possible to electro-elute the protein-containing solution 23 through the filters onto the protease-containing cleavage membrane 13, and thence onto the capture membrane 14. The protein-containing solutions 23 may be any solution containing one or more proteins including cell and tissue lysates, fractions collected from liquid chromatography including affinity and capillary electrochromatography or capillary electrophoresis separations that could be placed in the filter plate 24. Alternatively, if desirable, the proteins could be absorbed onto a solid phase resin to facilitate buffer exchange into an appropriate buffer prior to electroblotting. The bubbles that are initially trapped beneath the filters could be removed by positive pressure from below using excess transfer buffer to initiate electrical contact. After the transfer is complete, the mass spectrometer could be focused on those areas of the capture membrane 14 that were aligned with the outlets of each filter. A very similar setup can be implemented if the proteins are initially trapped within pieces of polyacrylamide 21, as after excision of protein-containing bands or spots from traditional 1 or 2-dimensional gels. In this case, the upper electrode manifold 25 could be equipped with small orifices designed to provide some back pressure to facilitate the task of eliminating trapped bubbles by applying pressure from beneath the filter plate 24.

Optionally, any combination of the components may be used together or separately, especially any one of the following: matrix-forming reagent for MALDI-TOF, electroblotting buffer, protease cleavage layers, collection layer(s), preferably composite capture layer(s) comprising a membrane(s) pretreated with polymers such as nitrocellulose and MALDI matrices, and PAGE materials. Other optional components could include microtiter filter plates and electrode manifolds to facilitate electro-blotting from said microtiter plates. Kits comprising the membranes and any one, two or more of the above optional components are hereby specifically declared to be within the scope of this invention. The components of the kit may be supplied in separate containers, but packaged overall as a kit.

In another aspect of the invention, an intermediate affinity capture membrane is placed between the digestion membrane and the capture membrane. This intermediate membrane captures a subset of the electroblotted peptides, for example, the subset of those peptides that are modified with biotin. These peptides are then released from the intermediate membrane and transferred to a second capture membrane in a second round of electroblotting. The selection of a sub-set of peptides is based on their interactions with specific reagents such as antibodies, streptavidin, metal chelation, DNA, RNA and PNA. For example, proteins are labeled with ICAT reagents (containing biotin) prior to separation by 1D or 2D gel electrophoresis. Upon electroblotting the separated proteins and concomitant enzymatic cleavage using the immobilized trypsin on the hydrophilic membrane, the resultant peptides containing biotin may be selected on an intermediate membrane to which streptavidin is immobilized. The non-biotin containing peptides migrate to a nitrocellulose/matrix modified capture membrane for analysis. By replacing the modified capture membrane with a new second modified capture membrane and altering the electroblotting conditions (i.e., change in buffer or pH), the biotin-containing peptides are removed from the intermediate streptavidin membrane and captured on the new modified capture membrane for mass analysis. This selection of specific peptides based on their physical and chemical characteristics allow for the sub-fractionation of these peptides in a two step process isolating ICAT reagent labeled peptides for identity and relative quantification.

The following Examples illustrate the invention. The words "Immobilon", "Trans-Blot" and "Voyager" are trademarks.

EXAMPLES

Materials and Methods

Chemicals. Gelman US450 membranes comprising polyethersulfone were purchased from Pall Life Sciences (Ann Arbor, Mich.). Low range SDS-PAGE standard PVDF membranes were purchased from Bio-Rad (Richmond, Calif., USA). Trifluoroacetic acid (TFA), Tris and trypsin were purchased from Sigma (St-Louis, Mo., USA). The trypsin was from bovine pancreas and was treated with L-1-Tosylamide-2-phenylethyl chloromethyl ketone (TPCK) to reduce the chymotrypsin-like activity that is usually present in trypsin. Acetonitrile (HPLC grade), calcium chloride, ethanolamine, glycine and L-BAPNA (N-Benzoyl-L-arginine-4-nitroanilide hydrochloride) were also purchased from Sigma.

1-D and 2-D PAGE. For the 1-D PAGE method, a Mini-Protean II electrophoresis apparatus (Bio-Rad, Richmond, Calif., USA) was used. SDS-PAGE was conducted essentially according to the method of as described by Laemmli, Nature 277: 680–685 1970, with a 10% polyacrylamide gel from BioRad. A mini whole gel eluter (Bio-Rad) was used to recover electroeluted proteins The protein samples used were wide-range SDS-PAGE standards from Sigma. They were soybean trypsin inhibitor (20.1 kDa), bovine carbonic anhydrase (28.9 kDa), chicken ovalbumin (42.7 kDa), bovine serum albumin (66.4 kDa), $E.\ coli$ beta-galactosidase (116 kDa) and myosin (205 kDa). FITC-BSA was made fluorescent by labeling with fluorescein isothiocyanate. FITC-labeled BSA was used to qualitatively and quantitatively assess the digestion and transfer of the protein after exposure to gel electrophoresis. Protein migration was carried out on a single lane at 100 V for 60–90 minutes.

Covalent attachment of trypsin and blockage of the Gelman US450 membrane. Benzamidine HCl (2 mg/ml), TPCK treated trypsin (1 mg/ml), and $NaBH_3CN$ (10 mg/ml) were dissolved in 0.5 M $Na_2SO_4$, 100 mM $Na_2HPO_4$, pH 7.4 to coat 0.1 ml per $cm^2$ of Gelman/Pall US450 polyethersulfone membrane. This aldehyde activated membrane is a recently introduced, commercially available modified polyethersulfone membrane. These groups are reactive towards nucleophiles such as amine groups from proteins or peptides. An equal volume of 1.5 M $Na_2SO_4$, 100 mM $Na_2HPO_4$, pH 7.4 buffer was added, and was allowed to react at RT for 16–18 hours with rocking at 75 rpm. Capping was accomplished by the addition of 0.2 M Tris and 5 mg/ml $NaBH_3CN$. The membranes were stored wet and refrigerated, or were dried using glycerol solution.

Trypsin Activity measurement: BAPNA assay: An 8 mm diameter disk of trypsin digestion membrane (0.5 $cm^2$) was added to 3 ml of 0.92 mM BAPNA, and incubated for 30 min at RT on an orbital mixer. The reaction was quenched with 0.5 ml of 30% acetic acid, and the trypsin activity was monitored at 410 nm, and compared to solutions of known trypsin activity.

Preparation of the composite membrane capture membrane: Immobilon CD, which is a PVDF membrane containing quaternary ammonium functional groups and is available from Millipore Corporation (Bedford, Mass.) was soaked in a solution of 20 mg/ml nitrocellulose, 10 mg/ml HCCA, 50% isopropanol, and 50% acetone. The membrane was then dried completely and re-wetted in transblotting buffer (described below).

The transblotting buffer used was 12 mM Tris(hydroxymethyl)aminomethane, 100 mM glycine, and 0.01% SDS, pH 8.3. Blotting was done on a Mini-Trans-Blot electrophoretic transfer cell (Bio-Rad, Redmond, Calif., USA) for 3 to 3.5 hours at 6 to 7V at room temperature.

Transblotting protocol: To perform the enzymatic digestion of the protein during the electroblotting, up to seven layers of -trypsin immobilized membrane were placed between the polyacrylamide gel (the protein source) and the composite capture membrane as the collecting surface to create a transblot-digestion sandwich (FIGS. 1 and 2a and b). After the electroblotting transfer procedure, the composite collection membranes, on which the fragments of digested protein were collected, were washed in deionized water for 10 to 30 minutes prior to MS analysis.

Preparation of the membrane prior to MALDI-TOF Analysis: Small pieces of the composite capture membrane (1×1 mm) and larger pieces (at least 40 mm square) containing the area of interest were cut from the composite capture collection membrane and fixed on an adaptable sample MALDI plate with a curable glue or silicone vacuum grease. Additional matrix was applied to the capture membrane as follows: 1 microliter of 10 mg per ml HCCA in 50% acetonitrile, 0.1% TFA solution was added to the anodic composite capture membrane, or alternatively, the additional matrix solution was sprayed onto the capture membrane before it was attached to the MALDI plate.

MALDI-TOF equipment and experimental conditions: The composite membranes were analyzed with a MALDI-TOF mass spectrometer Voyager STR or a Voyager DE-PRO (Applied Biosystems, Framingham, Mass., USA) equipped with a 337 nm nitrogen laser. The analyzer was used in the reflector mode at an accelerating voltage of 20 kV, a delay time of ion extraction of 125 ns and a low mass gate fixed at 800 Da. Laser power was set slightly above the threshold for molecular ion production. Spectra were obtained by summation of 10 to 1000 consecutive laser shots without any smoothing procedure (FIG. 4). For FIG. 6a, the spectra were acquired on a QSTAR PULSAR hybrid Q-TOF MS (Applied Biosystems) interfaced with an orthogonal MALDI ion source; for FIG. 6b, the spectra were acquired on a 4700 Protein Analyzer (Applied Biosystems).

Procedure

1) First run the 1D or 2D gel
2) Soak the gel, cleavage membrane, capture membrane and filter paper pads in the transfer buffer for 2–5 minutes
3) Prepare a sandwich starting from the bottom layer on the anode in the following order: filter paper pad, capture membrane, cleavage membrane(s), gel, filter paper pad
4) Assemble and transfer at 7V for 3.5 hours
5) Disassemble, rinse capture membrane with water, dry spray with matrix solution
6) Dry capture membrane and apply to MALDI plate with vacuum grease
7) Scan in MALDI-TOF MS (~20 minutes per lane to take 161 spectra at 250 um resolution with 20 Hz laser)

Results

Trypsin was attached covalently to Gelman US450 aldehyde activated membranes. The surface enzyme density was determined by a BAPNA test to be from 4.6–10.9 micrograms of active trypsin per square centimeter. The activity of the trypsin-bound Gelman US450 membranes remained stable when they were stored in the Tris-HCl/CaCl$_2$/NaN$_3$ solution containing 20% glycerol at 4° C. for periods of up to a month.

Experiments wherein two or more trypsin-bound membranes were interposed, one on top of another, between the polyacrylamide gel and the anodic composite capture membrane showed no obvious loss of protein nor loss of resolution during the electro-transfer procedures.

Figure 10:
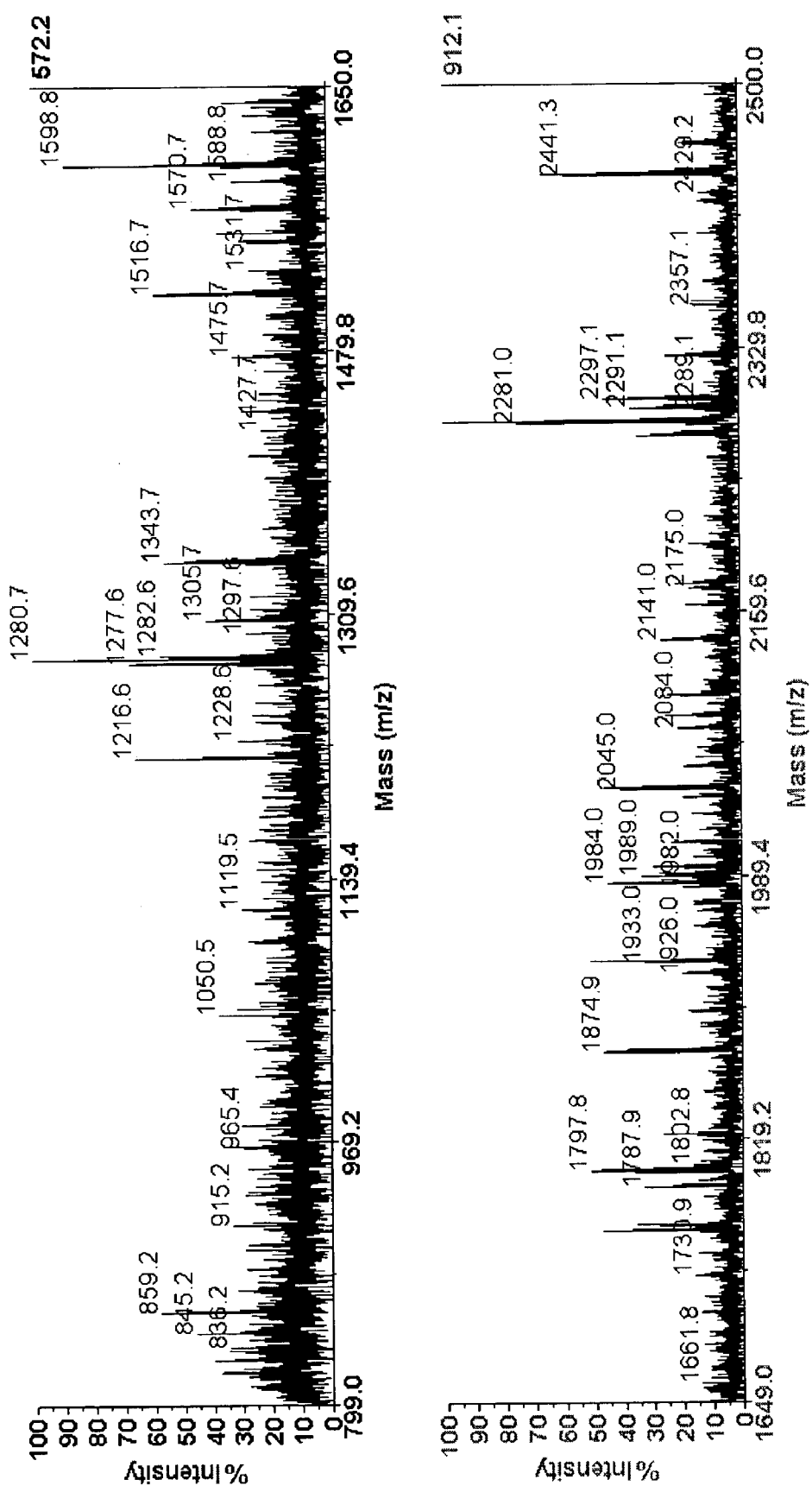
FIG. 10 is a MALDI-TOF MS spectrum of peptides found at position #92 of a 1D gel of *E. coli* lysate.

FITC-labeled BSA was used to qualitatively and quantitatively assess the digestion and transfer of the protein after exposure to gel electrophoresis. After SDS-PAGE separation, four proteins, bovine serum albumin (BSA), chicken ovalbumin, bovine carbonic anhydrase, and myosin run on the same track in the SDS-PAGE, were transblotted through up to seven trypsin-bound membranes onto a polyethersulfone membrane. An example is shown in FIGS. 3a and 3b. The above proteins were correctly identified from the MALDI-TOF MS (Voyager STR) spectra of their peptide fragments when automatically interpreted with Protein Prospector. An E. coli lysate was separated using 1D gel electrophoresis and analyzed at various positions on the capture membrane by MALDI-TOF mass spectrometry after electroblotting and digestion using the method and apparatus described in this invention. A representative spectrum and peptide identification data collected at position #92 of the gel (relative distance from the origin on a capture membrane) are shown in FIG. 10 and Table 1, respectively using ChemApplex software as described in co-pending U.S. patent application Ser. No. 09/745,920. Proteins that were identified by ChemApplex software at position #92 are listed in Table 2. A chicken heart was frozen and a cross sectional slice was obtained with a razor blade. The tissue was placed directly on the cleaving membrane and the "sandwich" was assembled as described above. The capture membrane was scanned and the distribution of two peptide ions is shown in FIGS. 8a and 8b.

TABLE 1

Peptides Identified from Position #92

| # | acc | accM | #m | #r | int | tri | ch | theo | maldi | ppm | < | sequence | > | mod | p |
|---|---|---|---|---|---|---|---|---|---|---|---|---|---|---|---|
| 1 | P04475 | | 1 | 53 | 106 | 318 | 100.0 | 1050.49 | 1050.52 | 33 | R | FQDEEVQR | D | | 0 |
| 1 | P04475 | | 1 | 11 | 382 | 7646 | 100.0 | 1277.64 | 1277.64 | 0 | R | NQGDHLLHSTR | K | | 0 |
| 1 | P04475 | | 0 | 81 | 62 | 0 | 0.3 | 1427.79 | 1427.73 | -45 | K | MAPPQISAEVLKK | M | 2 1 1SO | 1 |
| 1 | P04475 | | 1 | 15 | 331 | 6620 | 100.0 | 1598.83 | 1598.83 | -1 | K | SLGQFNLDGINPAPR | G | | 0 |
| 1 | P04475 | | 1 | 12 | 350 | 132 | 16.8 | 1983.95 | 1984.04 | 44 | R | FQDEEVQRDVSIMPFK | I | 1 1SO | 1 |
| 1 | P04475 | | 1 | 1 | 1291 | 17230 | 100.0 | 2281.04 | 2281.02 | -7 | R | TFEVLATNGDTHLGGEDFDSR | L | | 0 |
| 1 | P04475 | | 1 | 52 | 108 | 28 | 8.6 | 2423.28 | 2423.20 | -33 | R | KDVNPDEAVAIGAAVQGGVLTGDVK | D | 2 1 | 1 |
| 1 | P04475 | | 1 | 2 | 968 | 11800 | 100.0 | 2441.29 | 2441.27 | -8 | K | VALQDAGLSVSDIDDVILVGGQTR | M | | 0 |
| 2 | P05825 | | 2 | 10 | 384 | 686 | 20.0 | 1516.71 | 1516.73 | 11 | R | GDTSWVPPEMIER | I | | 0 |
| 2 | P05825 | P37028 | 7 | 50 | 123 | 17 | 2.0 | 1706.77 | 1706.80 | 15 | R | EDLSMQTTFTWYGK | Q | 1 | 0 |
| 2 | P05825 | | 2 | 13 | 345 | 6820 | 100.0 | 1787.86 | 1787.87 | 5 | R | TNFSLTGPLGDEFSFR | L | | 0 |
| 2 | P05825 | | 2 | 3 | 687 | 8882 | 100.0 | 1797.83 | 1797.84 | 8 | K | TQADAWDINQGHQSAR | A | | 0 |
| 2 | P05825 | P04475 | 1 | 12 | 350 | 818 | 20.0 | 1984.05 | 1984.04 | -9 | R | GMGPENTLILIDGKPVSSR | N | 1 | 0 |
| 2 | P05825 | | 2 | 40 | 157 | 3142 | 100.0 | 2092.11 | 2092.10 | -2 | R | LSIIPEYTLNSTLSWQAR | E | | 0 |
| 2 | P05825 | | 2 | 23 | 260 | 2488 | 100.0 | 2104.92 | 2104.94 | 10 | R | QGNLYAGDTQNTNSDSYTR | S | | 0 |
| 3 | Z00760 | | 3 | 46 | 138 | 3227 | 400.0 | 2163.06 | 2163.02 | -17 | R | LGEDNINVVEGNEQFISASK | S | | 0 |
| 3 | Z00760 | | 3 | 8 | 467 | 4374 | 160.0 | 2273.16 | 2273.12 | -17 | K | SIVHPSYNSNTLNNDIMLIK | L | | 0 |
| 3 | Z00760 | | 3 | 24 | 256 | 3773 | 200.0 | 2289.16 | 2289.12 | -14 | K | SIVHPSYNSNTLNNDIMLIK | L | Ox | 0 |
| 3 | Z00760 | P08577 | 9 | 14 | 336 | 20 | 1.0 | 2291.16 | 2291.12 | -17 | | g | | | 0 |
| 4 | P09373 | | 4 | 51 | 111 | 515 | 100.0 | 828.43 | 828.41 | -22 | K | IFTEYR | K | | 0 |
| 4 | P09373 | | 4 | 16 | 304 | 6089 | 100.0 | 1216.57 | 1216.58 | 3 | K | GDWQNEVNVR | D | | 0 |
| 4 | P09373 | | 4 | 6 | 527 | 4712 | 44.7 | 1280.67 | 1280.67 | -3 | R | LREEIAEQHR | A | | 1 |
| 4 | P09373 | | 4 | 27 | 214 | 1000 | 100.0 | 1305.68 | 1305.71 | 21 | K | SGVLTGLPDAYGR | G | | 0 |
| 4 | P09373 | | 0 | 34 | 196 | 1 | 0.1 | 1342.63 | 1342.67 | 36 | K | MIEGSCKAYNR | E | 1 1ACR | 1 |
| 4 | P09373 | | 4 | 33 | 200 | 1163 | 100.0 | 1343.69 | 1343.66 | -17 | R | TSTFLDVYIER | D | | 0 |
| 4 | P09373 | P06959 | 8 | 36 | 173 | 2 | 0.2 | 1639.82 | 1639.79 | -18 | R | EEIAEQHRALGQMK | E | 1 | 1 |
| 4 | P09373 | | 4 | 4 | 587 | 5240 | 100.0 | 1874.94 | 1874.92 | -11 | K | THNQGVFDVYTPDILR | C | | 0 |
| 4 | P09373 | | 4 | 22 | 263 | 104 | 10.0 | 1932.91 | 1932.95 | 25 | K | ITEQEAQEMVDHLVMK | L | 1 2SO | 1 |
| 4 | P09373 | | 0 | 59 | 86 | 5 | 0.4 | 1993.95 | 1993.97 | 7 | K | SEPIKGDVLNYDEVMER | M | 1 | 1 |
| 4 | P09373 | | 0 | 32 | 200 | 12 | 2.0 | 2009.95 | 2010.02 | 33 | K | SEPIKGDVLNYDEVMER | M | 1 1SO | 1 |
| 4 | P09373 | P08577 | 9 | 14 | 336 | 20 | 0.7 | 2291.14 | 2291.12 | -11 | R | EMLLDAMENPEKYPQLTIR | V | 1 | 1 |
| 4 | P09373 | | 4 | 9 | 414 | 1600 | 28.8 | 2296.15 | 2296.13 | -7 | K | DGISYTFSIVPNALGKDDEVR | K | 1 | 1 |
| 4 | P09373 | | 4 | 21 | 277 | 2271 | 100.0 | 2460.27 | 2460.24 | -12 | K | LAQFTSLQADLENGVNLEQTIR | L | | 0 |
| 5 | P27302 | P04475 | 1 | 11 | 382 | 6156 | 100.0 | 1277.64 | 1277.64 | -6 | R | FEAYGWHVIR | D | | 0 |
| 5 | P27302 | | 5 | 45 | 138 | 432 | 100.0 | 1282.61 | 1282.65 | 32 | K | AYPQEAAEFTR | R | | 0 |
| 5 | P27302 | | 5 | 66 | 77 | 11 | 2.9 | 1297.65 | 1297.62 | -22 | R | DIDGHDAASIKR | A | 1 | 1 |
| 5 | P27302 | | 5 | 69 | 74 | 271 | 100.0 | 1321.60 | 1321.64 | 27 | K | HNPQNPSWADR | D | | 0 |
| 5 | P27302 | | 5 | 43 | 144 | 1206 | 100.0 | 1762.85 | 1762.83 | -12 | K | AINEDAAGNYIHYGVR | E | | 0 |
| 5 | P27302 | | 0 | 86 | 58 | 12 | 1.0 | 1933.95 | 1933.94 | -5 | K | FAAYAKAYPQEAAEFTR | R | 1 | 1 |
| 5 | P27302 | | 5 | 25 | 236 | 1742 | 100.0 | 1988.98 | 1988.95 | -14 | K | AGTHDSHGAPLGDAEIALTR | E | | 0 |
| 6 | P02996 | | 6 | 67 | 77 | 16 | 10.0 | 1098.55 | 1098.49 | -49 | K | GYEFINDIK | G | 1 | 0 |
| 6 | P02996 | | 6 | 18 | 285 | 2170 | 100.0 | 1597.84 | 1597.86 | 13 | K | IATDPFVGNLTFFR | V | | 0 |

TABLE 1-continued

Peptides Identified from Position #92

| # | acc | accM | #m | #r | int | tri | ch | theo | maldi | ppm | < | sequence | > | mod | p |
|---|---|---|---|---|---|---|---|---|---|---|---|---|---|---|---|
| 6 | P02996 | | 6 | 30 | 205 | 1163 | 100.0 | 1820.93 | 1820.96 | 18 | R | EFNVEANVGKPQVAYR | E | 1 | 0 |
| 6 | P02996 | | 6 | 29 | 205 | 1169 | 100.0 | 2058.98 | 2059.02 | 18 | K | VEVETPEENTGDVIGDLSR | R | | 0 |

TABLE 2

Proteins Identified from Position #92

| # | acc | Protein | mw | m | Tri | % Ch | % I | ppw |
|---|---|---|---|---|---|---|---|---|
| 1 | P04475 | Dnak | 68992 | 7 | 501 | 24 | 20 | 12 |
| 2 | P05825 | ferrienterobactin receptor | 82112 | 5 | 451 | 18 | 10 | 8 |
| 3 | Z00760 | bovine trypsin | na | 3 | 404 | 60 | 5 | 16 |
| 4 | P09373 | formate acetyltransferase 1 | 85234 | 9 | 378 | 20 | 16 | 12 |
| 5 | P27302 | transketolase 1 | 72211 | 5 | 33 | 21 | 4 | 19 |
| 6 | P02996 | elongation factor g | 77458 | 4 | 31 | 17 | 4 | 19 |
| | | Sum | | | | | 59 | |

Where the column headings in Tables 1 and 2 are represented by the following:

Table 1

| | |
|---|---|
| # | protein list order |
| acc | Swiss Prot accession number |
| accM | Alternative SwissProt accession number (to a lower ranking protein) |
| #m | protein list number for alternative accession number |
| #r | rank of the mass sorted by intensity; 1 is the most intense mass |
| int | intensity of the mass |
| tri | A composite score for the match combining intensity, ChemScore and mass error at the peptide level |
| ch | ChemScore of the peptide |
| theo | molecular weight of the peptide based on its sequence |
| maldi | measured molecular weight of the mass |
| ppm | error in parts per million between "theo" and "maldi" |
| < | amino acid immediately preceding the proposed peptide in the protein sequence |
| sequence | sequence of the peptide |
| > | amino acid after the peptide in the protein sequence |
| mod | abbreviation for modification to residues in the peptide |
| p | number of trypsin missed cleavages in the peptide |

Table 2

| | |
|---|---|
| # | protein list order |
| acc | Swiss Prot accession number |
| protein | name of the protein |
| mw | molecular weight of the protein |
| m | number of matched peptides to the protein |
| tri | A composite score for the match combining intensity, ChemScore and mass error at the protein level. |
| %Ch | percent ChemScore matched for the protein |
| % I | percent intensity matched |
| ppw | intensity-weighted average ppm error for the matched peptides |

What is claimed is:

1. A method for identifying or quantifying polypeptides from a protein sample, comprising:
   (a) separating polypeptides from said protein sample to provide a support containing said polypeptides;
   (b) providing at least one digestion membrane adjacent to said support and on which is immobilized at least one polypeptide cleavage reagent in an amount effective for digesting substantially all of the polypeptides in said sample after a single pass of said polypeptides through said membrane;
   (c) providing at least one capture membrane, downstream, in the direction of migration of peptide fragments of said polypeptides during electroblotting, from said at least one digestion membrane;
   (d) applying prior to step (e) a MALDI matrix material to the capture membrane;
   (e) electroblotting said polypeptides from said support through said at least one digestion membrane;
   (f) collecting said fragments on said at least one capture membrane; and
   (g) identifying or quantifying said collected fragments by MALDI-TOF mass spectrometry.

2. The method of claim 1, further comprising identifying the polypeptide from which said fragments originated.

3. The method of claim 1, wherein said support is an electrophoresis gel.

4. The method of claim 1, further comprising modifying said capture membrane to promote peptide capture by adding thereto nitrocellulose.

5. The method of claim 1, wherein said MALDI matrix material comprises alpha cyano-4-hydroxycinnamic acid.

6. The method of claim 1, further comprising labeling said protein sample with heavy stable isotopes prior to separation into said polypeptides.

7. The method of claim 1, wherein said cleavage reagent is covalently bonded to said digestion membrane.

8. The method of claim 7, wherein said digestion membrane is selected from the group consisting of a modified PVDF membrane and a modified polyethersulfone membrane, and wherein said cleavage reagent is a protease.

9. The method of claim 8, wherein said protease is trypsin.

10. The method of claim 1, wherein said cleavage reagent is immobilized on said digestion membrane in said effective amount by the following steps:
   reacting a salt, a protease inhibitor and said cleavage reagent with said membrane to produce a Schiff base;
   reducing said Schiff base with a reducing agent; and
   removing said protease inhibitor from said membrane.

11. The method of claim 10, further comprising capping residual active groups on the surface of said membrane.

12. The method of claim 1, further comprising focusing the capture of said fragments onto a discrete zone of said capture membrane.

13. The method of claim 1, further comprising providing an intermediate capture membrane between said digestion membrane and said capture membrane to capture a subset of said polypeptides.

14. The method of claim 13, further comprising releasing said captured subset of polypeptides and electroblotting said subset to a second capture membrane.

15. The method of claim 1, wherein said support is devoid of a cleavage reagent.

16. The method of claim 1, wherein there are a plurality of adjacent digestion membranes.

* * * * *